US011357585B2

(12) United States Patent
Simi et al.

(10) Patent No.: US 11,357,585 B2
(45) Date of Patent: Jun. 14, 2022

(54) ROBOTIC MICROSURGICAL ASSEMBLY

(71) Applicant: MEDICAL MICROINSTRUMENTS S.P.A., Pisa (IT)

(72) Inventors: Massimiliano Simi, Pisa (IT); Giuseppe Maria Prisco, Pisa (IT)

(73) Assignee: MEDICAL MICROINSTRUMENTS S.P.A., Pisa (IT)

( * ) Notice: Subject to any disclaimer, the term of this patent is extended or adjusted under 35 U.S.C. 154(b) by 280 days.

(21) Appl. No.: 16/605,107

(22) PCT Filed: Apr. 13, 2018

(86) PCT No.: PCT/IB2018/052590
§ 371 (c)(1),
(2) Date: Oct. 14, 2019

(87) PCT Pub. No.: WO2018/189721
PCT Pub. Date: Oct. 18, 2018

(65) Prior Publication Data
US 2021/0121256 A1    Apr. 29, 2021

(30) Foreign Application Priority Data

Apr. 14, 2017    (IT) .................. 102017000041980

(51) Int. Cl.
*A61B 34/37*     (2016.01)
*A61B 34/00*     (2016.01)
*A61B 34/30*     (2016.01)

(52) U.S. Cl.
CPC .............. *A61B 34/37* (2016.02); *A61B 34/71* (2016.02); *A61B 2034/306* (2016.02)

(58) Field of Classification Search
CPC ... A61B 34/37; A61B 34/71; A61B 2034/306; A61B 2017/2926; A61B 34/72; A61B 2017/00323
See application file for complete search history.

(56) References Cited

U.S. PATENT DOCUMENTS 5,710,870 A    1/1998  Ohm et al.
6,371,952 B1   4/2002  Madhani et al.
(Continued)

FOREIGN PATENT DOCUMENTS

EP    2 415 418 A1    2/2012
WO    03/001986 A2    1/2003
(Continued)

OTHER PUBLICATIONS

International Search Report and Written Opinion of the International Searching Authority for International Patent Application No. PCT/IB2018/052590 dated Jun. 5, 2018, 10 pages.

*Primary Examiner* — Gary Jackson
*Assistant Examiner* — Sebastian X Lukjan
(74) *Attorney, Agent, or Firm* — Merchant & Gould P.C.

(57) ABSTRACT

A robotic microsurgery assembly (1) includes at least one master tool (2) to detect a manual command; at least one slave manipulator (3); and at least one surgical instrument (70) operated on by the one slave manipulator (3). At least one control unit (4) receives at least a first command signal including information about the manual command and sends a second command signal to at least one actuator to control the slave manipulator (3). The surgical instrument includes at least one jointed subassembly (5). The jointed subassembly (5) includes a first link (6), a second link (7), and a third link (8). The first link structural body (9) and the second link structural body (10) have at least one tendon contact surface (18), avoiding the at least one tendon contact surface (18) being a hole surface.

13 Claims, 22 Drawing Sheets

(56) References Cited

U.S. PATENT DOCUMENTS

| | | | |
|---|---|---|---|
| 6,385,509 B2 | 5/2002 | Das et al. | |
| 6,394,998 B1 | 5/2002 | Wallace et al. | |
| 6,676,684 B1 | 1/2004 | Morley et al. | |
| 6,840,938 B1 | 1/2005 | Morley et al. | |
| 6,963,792 B1 | 11/2005 | Green | |
| 7,155,316 B2 | 12/2006 | Sutherland et al. | |
| 2002/0128661 A1* | 9/2002 | Brock | A61B 34/37 606/130 |
| 2003/0034748 A1 | 2/2003 | Walters et al. | |
| 2003/0135204 A1 | 7/2003 | Lee et al. | |
| 2008/0177285 A1 | 7/2008 | Brock et al. | |
| 2009/0105715 A1* | 4/2009 | Belliard | A61B 17/707 606/103 |
| 2009/0112230 A1 | 4/2009 | Jinno | |
| 2012/0289946 A1* | 11/2012 | Steger | A61B 17/29 606/1 |
| 2013/0302876 A9 | 11/2013 | Khan | |
| 2014/0135794 A1 | 5/2014 | Cau | |
| 2016/0051274 A1 | 2/2016 | Howell et al. | |
| 2016/0302876 A1 | 10/2016 | Teichtmann | |
| 2017/0020615 A1 | 1/2017 | Koenig et al. | |

FOREIGN PATENT DOCUMENTS

| | | |
|---|---|---|
| WO | 2010/005657 A2 | 1/2010 |
| WO | 2010/009221 A2 | 1/2010 |
| WO | 2014/151952 A1 | 9/2014 |

\* cited by examiner

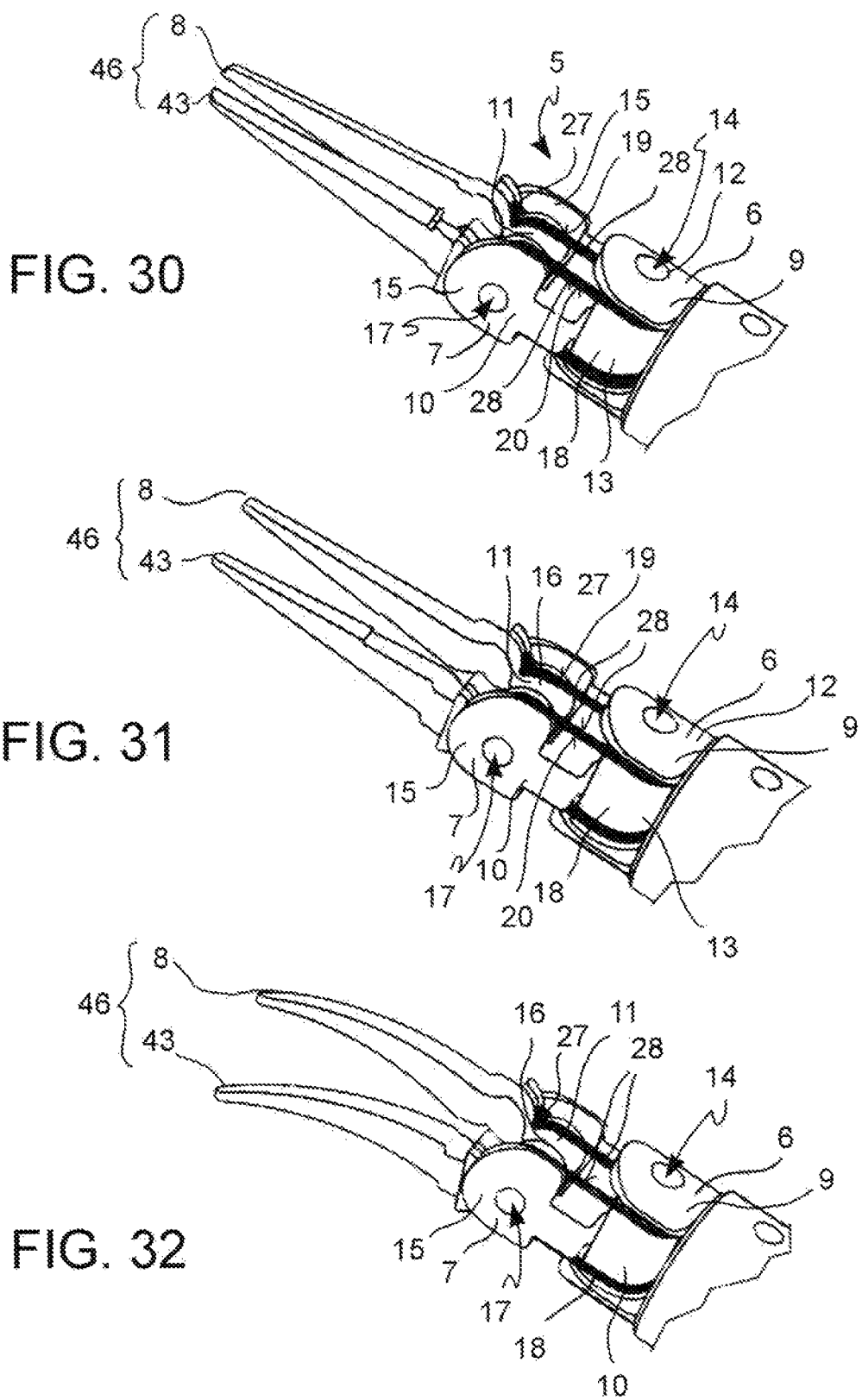

ROBOTIC MICROSURGICAL ASSEMBLY

This application is a National Stage Application of PCT/IB2018/052590, filed 13 Apr. 2018, which claims the benefit of Serial No. 10/2017000041980, filed 14 Apr. 2017 in Italy, and which applications are incorporated herein by reference. To the extent appropriate, a claim of priority is made to each of the above-disclosed applications.

FILED OF THE INVENTION

It is an object of the present invention a robotic surgical assembly.

In particular, the present invention relates to a robotic microsurgical assembly.

The present invention relates to a robotic microsurgical assembly of the type comprising a master tool and a surgical instrument.

The present invention relates to a surgical instrument as well as to a slave assembly for robotic surgery.

BACKGROUND

In robotically-assisted or robotic surgery under the master—slave paradigm, the surgeon typically operates a master tool to control the motion of surgical instruments. The master tool ("the master") detects motion of the surgeon's hand. The master tools can be connected to a master tool manipulator including actuators to provide positioning and force feedback on the master tool. The master tools are coupled to a slave manipulator ("the slave") including actuators, that manipulates, internally articulates and more generally operates the medical or surgical instruments. Such medical instruments can be connected and disconnected from the slave. A sterile barrier is usually provided between the slave and the medical instruments.

Robotic assemblies for surgery or microsurgery comprising multi-joint robotic arms operating surgical instruments are known in the field. For instance, document U.S. Pat. No. 7,155,316 discloses a robotic assembly for performing brain microsurgery under MRI (Magnetic Resonance Imaging) guidance comprising an MRI-based image acquisition system and two multi-joint arms, each with three rotary joints with vertical axes to avoid direct gravity loads (as shown for instance in FIG. 7 of said document U.S. Pat. No. 7,155,316), each connected to its respective end-effector endowed with an internal degree of freedom of motion for gripping.

It is also notable that the execution of the principal surgical primitives, such as tissue tensioning and anastomotic suturing, requires the ability to orient the surgical instrument tip in a large spatial cone of directions and to rotate the instrument around its longitudinal axis (roll), for example to guide the needle through the tissue with the tip of the needle holder instrument, in a similar manner as the human hand is jointed at the wrist and the elbow.

Robotic assemblies for surgery or microsurgery comprising a teleoperated master-slave system are generally known, as described, for example, in document U.S. Pat. No. 6,963,792 and, more specifically for the microsurgical application in U.S. Pat. No. 6,385,509 and US-2014-0135794, that describe kinematic solutions for the movement of the surgical instrument tip that require coordination of a plurality of joints in a serial kinematic chain that clutter the operating field. Such encumbrance effect is increasingly pronounced as the joints articulating the tip of the instrument are further away from the tip itself. Moreover said microsurgical systems do not allow adequate movement, and more specifically adequate reorientation, of the instrument tip when in an operating site inside a lesion as little as 10 centimeters from the surface of the skin.

The adoption of robotic technologies can bring about great benefits, allowing both a high degree of miniaturization of the instruments and scaling the size of the movements in the operating field, hence eliminating the effect of physiological tremor and easing the manual task. For example, microsurgical procedures are carried out in several phases of the reconstruction of biological tissues, such as for example in the execution of blood vessel anastomosis, comprising small diameter vessels and nerves. Such procedures are carried out to reconstruct anatomy after the occurrence of traumatic lesions or of lesions produced by surgical removal of tissue, to reattach limbs and to revascularize tissues, all performed in an open surgery set-up given the pre-existence of a superficial lesion.

Others examples of application of microsurgical techniques are found in transplant surgery, neurosurgery or in vascular surgery, as well as in surgery around and inside the eye, and in the inner ear, as in the case of cochlear implants. Also the prominent surgical procedure of cardiac by-pass comprises the critical step of anastomosis of the coronary arteries. The need for instrument miniaturization is also felt in other surgical techniques, for example in minimal invasive surgery, such as laparoscopy and endoscopy, that are aimed at limiting the invasiveness of surgical instruments on biological tissue. With reference to laparoscopy, the technical solutions known in the art do not allow a satisfactory miniaturization of the diameter of the laparoscopic instruments employed in Single Incision Laparoscopic Surgery or Single Port Surgery. Moreover, it is worth noticing that the endoscopes typically employed in minimally-invasive-surgery (MIS) have an instrument channel with a diameter between 1 and 3.2 millimeters. Such dimensions limit the functionality of current surgical instrumentation available through the endoscope instrument channel, which at present is typically just capable of gripping action.

Document U.S. Pat. No. 5,710,870 discloses an example of double-jointed joint which connects two adjacent robot members, and wherein such double-jointed joint is suitable for providing a single degree of freedom to said two adjacent robot members connected by means of said double-jointed joint.

Medical instruments comprising a jointed subassembly suitable to work on the patient are generally known in the art. For example, document WO-2010-009221 shows a robotic surgical instrument comprising a distally jointed subassembly, capable of providing three degrees of freedom of motion, respectively pitch, yaw and grip, employing four actuation cables. Such cables slide inside guiding channels, or sheaths, present inside the body of the articulating device.

Said technical solution limits the miniaturization of the robotic articulating device, because friction between the guiding channels surfaces and the cables that slide inside them limits the positioning precision achievable by the articulating device. As it is known in the art, as the physical dimensions of a medical instruments are reduced, difficulties arise which are related to the increase of relevance of superficial forces, such as friction, that become dominant over volume forces. Such a phenomenon requires to resort to solutions that minimize friction forces, and at the same time reduce lost motions of mechanics to a minimum.

The loss of positioning precision of an articulating device is a fundamental technological obstacle to further miniaturization of articulating instrument, since, with miniaturization, also the stiffness of the driving members (tendons) goes down with the second power of their diameter, making it even more difficult to overcome friction for the precise positioning of the instrument tip. Moreover such a solution requires a tendon guiding system comprising channels and guiding surfaces that surround the cables that make the pitch and yaw links, as well as the instrument shaft, very difficult to miniaturize using known fabrication methods, such as for example injection molding and machining, and would be prone to have several locations of mechanical weakness.

In order to simplify the miniaturization of a surgical instrument, said document WO-2010-009221 indicates the advantageous opportunity of reducing the number of actuation tendon terminations, associated to three degrees of freedom, from six to four, exploiting for actuation the torque that cables terminated on the yaw link apply on the pitch link (see FIG. 4-A of cited document) and requires to such purpose to pull and release selectively such cables, thanks to a kinematic mechanism comprising a number of gears. Moreover, the driving system described requires that each end of an actuation tendon is attached to a winch, that selectively winds the tendon inducing the pull.

The presence of mechanical aspects such as said winch and said teeth, which are notoriously subject to lost motion, creates a difficult to drive a miniature articulation, because lost motion in the drive system is translated into an angular play at the joint, that increase as the articulating device gets smaller. Said driving system is also unsuited to keep a low preload on the actuation cables to further limit friction and wear.

Moreover, the solutions described for tendon termination comprise tortuous paths meant to trap the tendon in some sections. Such solutions require the use of cables that are sufficiently resistant to survive such trapping, such as steel cables or cables with larger diameter than otherwise required.

For example, document US-2002-128661 shows actuation cables which are routed through guide holes provided for in the instrument shaft, wherein each of said actuation cables touches with a distal portion thereof a single link and it is firmly secured thereto. A further similar example is given by document U.S. Pat. No. 6,676,684.

Further examples of actuation cables for surgical instruments suited to slide, when pulled or pushed, inside sheaths or guiding channels, for example obtained on the lateral surfaces of pulleys, are disclosed in documents U.S. Pat. Nos. 6,371,952, 6,394,998 and WO-2010-005657.

Specifically, the latter document discloses a solution where actuation cables follow trajectories that cross as they go around pulleys that comprise guiding channels to avoid that such cables interfere with one another, a condition that limits their efficacy in transmitting motion to the articulating device, such as for instance in case of bundling up or sliding of one tendon onto another one. The provision of idle pulleys, necessarily with a diameter close to half of the instrument diameter (as shown in FIG. 4 of cited document WO-2010-005657) and attached to the links, and specifically to the main structural body of the links, for example to links integral with the instrument shaft, or to the pitch link, to guide the tendon to cross, is a considerable obstacle to miniaturization.

Moreover the provision of grooves and walls to realize the channels for the actuation cables is a further obstacle to the miniaturization of the shaft or cannula diameter of a medical, or surgical, instrument.

The document US-2003-0034748 discloses a solution suitable for reducing the diameter of the surgical instrument to 5.1 millimeters. This instrument foresees the use of a series of disks that function as vertebra, providing some bending at bending radius larger than the instrument diameter.

Nevertheless, this solution is not appropriate for achieving a compact joint that can extend for approximately one instrument diameter, or in other words, has a radius of curvature similar to its diameter. This is instead achievable by those articulations described in the documents cited above which are based on a pivot-type joint, comprised of a pure axis of rotation, for example implemented as pin joints, clevis, etc.

A further obstacle to the miniaturization of jointed or articulated devices is the challenge of fabricating and assembling three dimensional micromechanical parts with sufficient precision at a reasonable process cost. The need to develop relatively high forces at the tip in devices with a sub-millimeter size suggests the use extremely rigid metals for such components, such as for example tool steel.

Hence there is a felt need to provide a jointed or articulated medical instrument, or an assembly comprising an jointed or articulated device, which is structurally and functionally suitable for extreme miniaturization without compromising its reliability and safety.

There is also a felt need to provide a jointed or articulated medical instrument, or an assembly comprising a jointed device, suitable for carrying out a wide variety of medical-surgical therapies.

Then, there is a felt need to provide a jointed or articulated medical instrument, or an assembly comprising a jointed or articulated device, that is durable and able to undergo periodic maintenance without compromising its sterility or reliability.

There is a felt need to provide a jointed or articulated medical instrument, or an assembly comprising a jointed device, that requires simplified manufacturing and assembly compared to known solutions.

The need is felt to miniaturize medical instruments.

The need is felt to reduce the known dimensions of medical instruments.

For example, document WO-2014-151952 shows a medical instrument comprising a plurality of links forming a joined device, said medical instrument having actuation cables wrapping around a plurality of pulleys rotatably supported on shaft provided cantilevered on the links of the medical instrument. This solution is characterized by a high number of parts, and the layout of said pulleys provided on said shafts forces to machining said shaft to resist to the stresses arising from the use of the medical instrument, therefore this solution results unsuitable for miniaturization, in fact this device could not measure less than 10 millimeters in diameter. Similar solutions are shown, for example, in documents U.S. Pat. No. 6,676,684, US-2009-0112230 and US-2003-135204.

It is therefore felt the need of reducing the number of parts which forms the medical instrument.

For example, document WO-03-001986 shows a medical instrument comprising a plurality of disc-shaped links forming a joined device, wherein each of said links comprises a plurality of holes for guiding the actuation cables. Said holes keep the actuation cables within said links, avoiding that they depart from said links, avoiding that they take up space around the links and avoiding that they create pinch points, all such scenarios being unacceptable for surgical applications, for example for safety reasons. Said holes also guide the actuation cables avoiding that a mechanical advantage they have in applying a pull force to a said link is reduced when said actuation cables depart from said links.

Therefore, this solution is unsuitable for miniaturization as it is highly unsatisfactory performing micrometric holes in such links, and at the same time, it is unsatisfactory providing actuation cables which slide inside such holes without damaging.

It is therefore felt the need of obtaining an accurate guiding of the actuation cables without providing micrometric holes in the links and at the same time to reduce the number of parts which forms the medical instrument.

For example, document US-2008-177285 discloses a medical instrument comprising a plurality of links, wherein some links comprise two protruding pins suitable to guide the deflection of the actuation cables. Although satisfactory under some points of views, such solution is also unsuitable for miniaturizing, as the protruding pins dimension cannot be reduced without compromise the integrity of the links composing the medical instrument.

Therefore, the need is felt to provide a miniaturized medical instrument, having a plurality of links actuated by means of actuation cables, without compromise the structural resistance, and thus the safety when in use, of the medical instrument.

For example document US-2016-0051274 discloses a wrist mechanism (FIG. 15) including rolling element joints to provide improved miniaturization to instrument diameters between 1 and 5 millimeters. Such solution fails to provide an improved solution for the routing of actuation tendons, which are still guided through holes in the link members, which are difficult to miniaturize. The solution also requires sharp bends to the cables at the entrance and exit of said holes, creating points of weakness.

Similarly document US-2017-0020615 discloses a wrist subassembly (FIG. 5-A) with a reduces number of parts that fails to provide a solution to route the actuation tendons without the use of guide holes that are required to exert a large lateral force on the tendons to keep them on their path, creating likely points of weakness and friction for said tendons.

Similarly document EP-2415418, discloses a wrist subassembly (FIG. 4 and FIG. 5) including a double-joined joint, that provide advantages for the decoupled control of the wrist joints. The solution still relies on the employment of a number of guide idler pulleys to route the actuation cables, thus a large number of parts that are difficult to miniaturize and assemble.

Similarly, document US 2016-0302876 discloses a wrist subassembly (FIG. 1 and FIG. 2) including a double-jointed pitch joint connecting the first link to the second link. The proposed solution includes a pair of actuation tendons that are routed over a idler pulleys (reference numbers 54 and 58), which are pinned to the structural body of respectively link one and link two, to actuate the third (yaw) link. The presence of idler pulleys pinned to the structural link members limits the miniaturization of the instrument diameter due to the minimum diameter of available idler pulleys and weakness of their inner ring support.

Therefore, it is strongly felt the need to miniaturize surgical instruments for robotic surgery.

Solution

A scope of the invention described here is to overcome the limitations of known solutions as described above and to provide a solution to the needs mentioned with reference to the state of the art.

FIGURES

Further characteristics and advantages of the invention will appear from the description reported below of preferred embodiments, which are given as examples and are not meant to be limiting, which makes reference to the attached figures, in which:

FIGS. 30, 31 and 32 are perspective views of a jointed subassembly, according to some embodiments;

DETAILED DESCRIPTION OF SOME PREFERRED EMBODIMENTS

Figure 1:
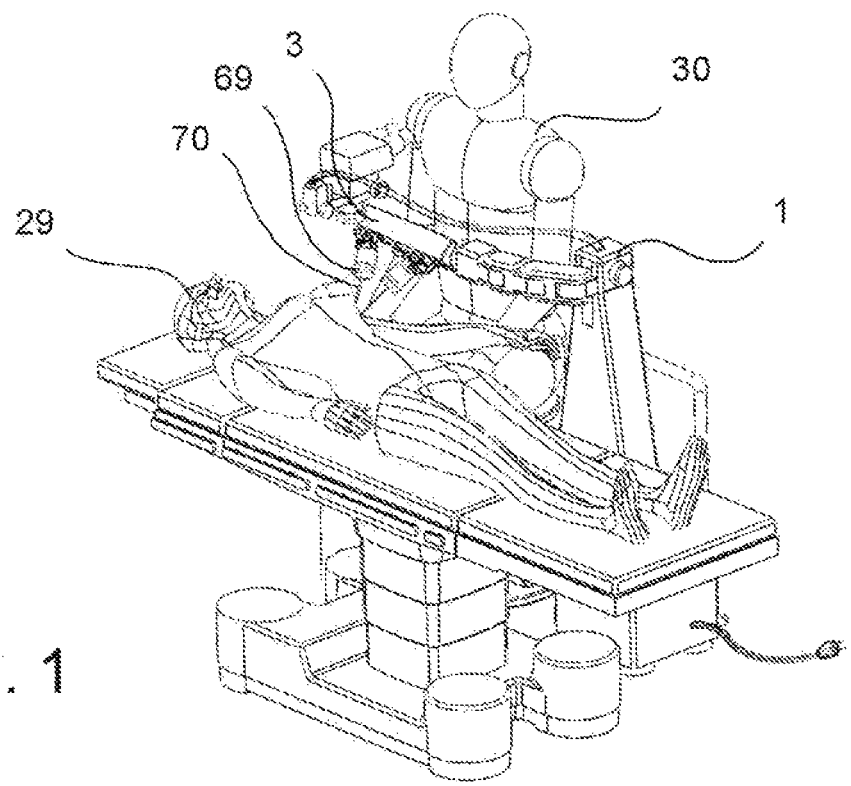
FIG. 1 is a perspective view of a robotic surgical assembly, according to an embodiment, wherein sketches depict a patient a surgeon.
Figure 2:
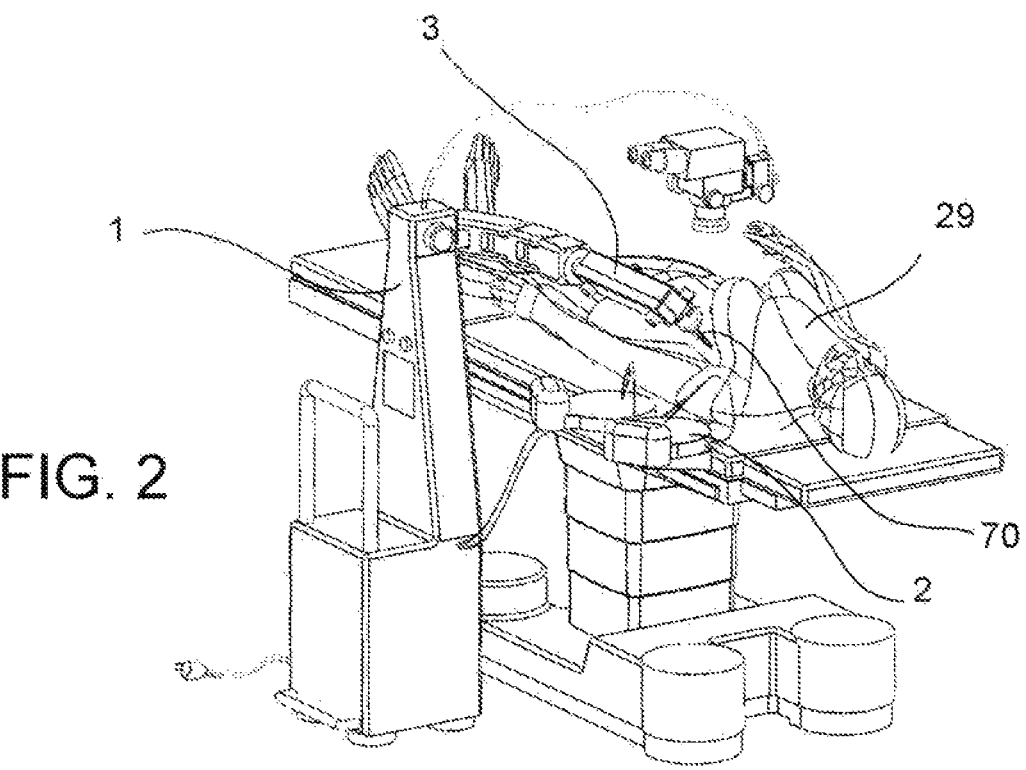
FIG. 2 is a perspective view of a robotic surgical assembly, according to an embodiment, wherein a sketch depicts a patient.
Figure 3A:
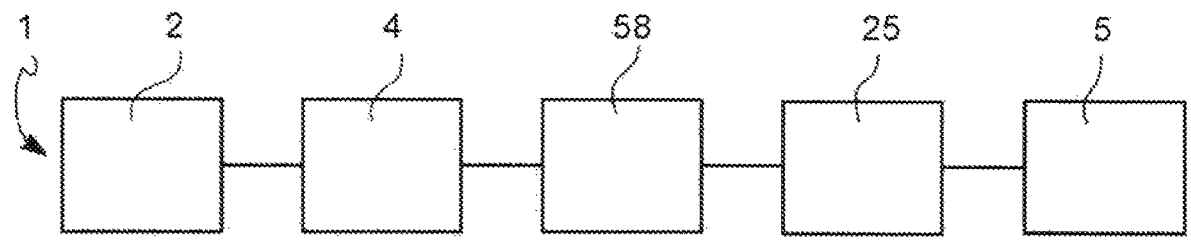
FIG. 3A is a block diagram of a robotic surgical assembly, according to an embodiment.
Figure 3B:
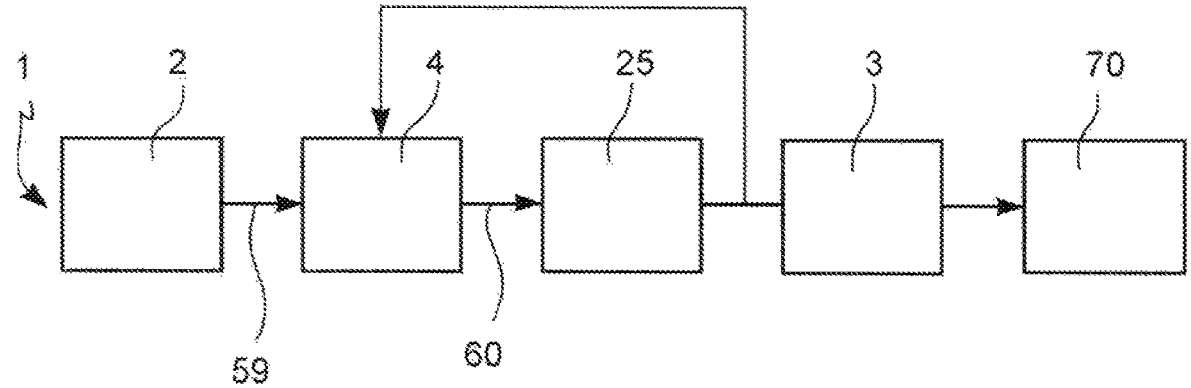
FIG. 3B is a block diagram of a robotic surgical assembly, according to an embodiment.
Figure 3C:
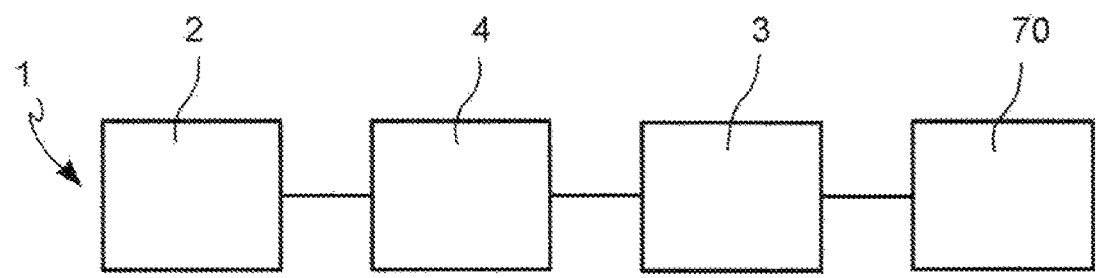
FIG. 3C is a block diagram of a robotic surgical assembly, according to an embodiment.
Figure 4:
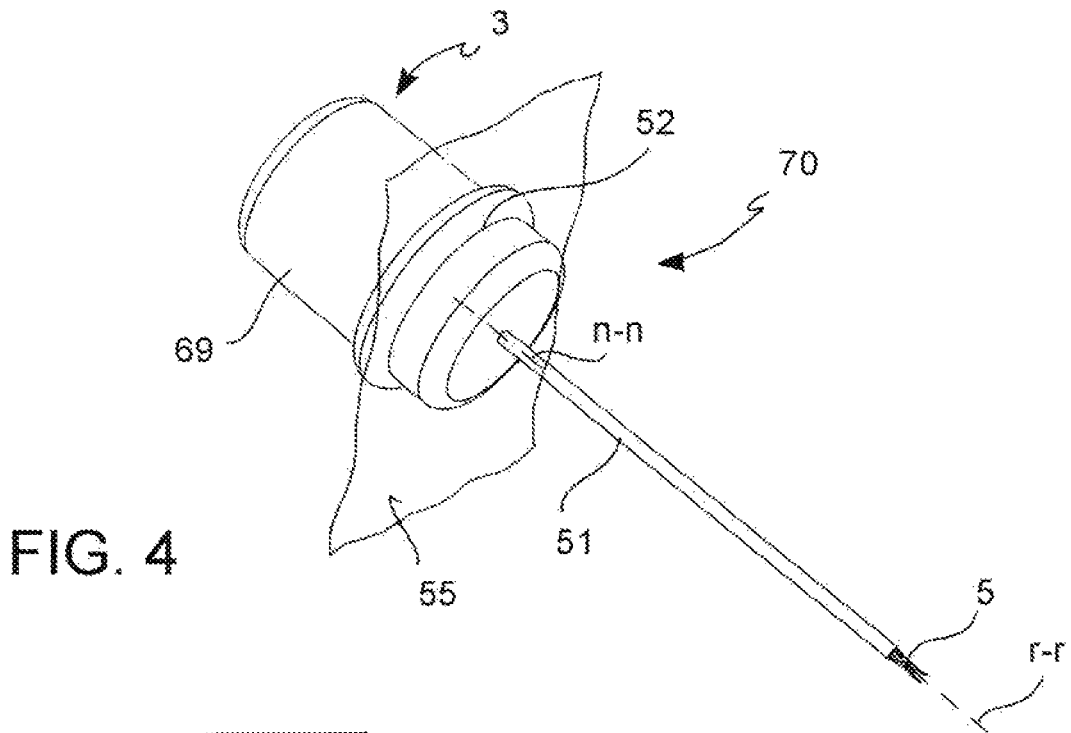
FIG. 4 is a perspective view of a portion of a slave manipulator connected to a surgical instrument, according to an embodiment.
Figure 5:
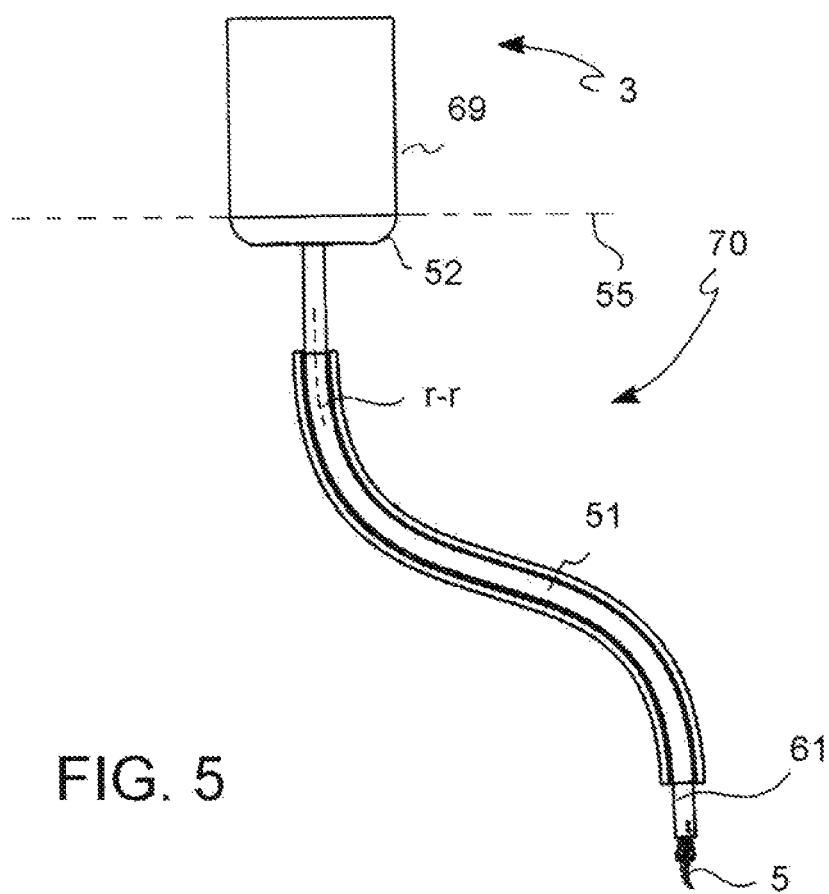
FIG. 5 is a plan view of a portion of a slave manipulator connected to a surgical instrument, according to an embodiment.
Figure 6:
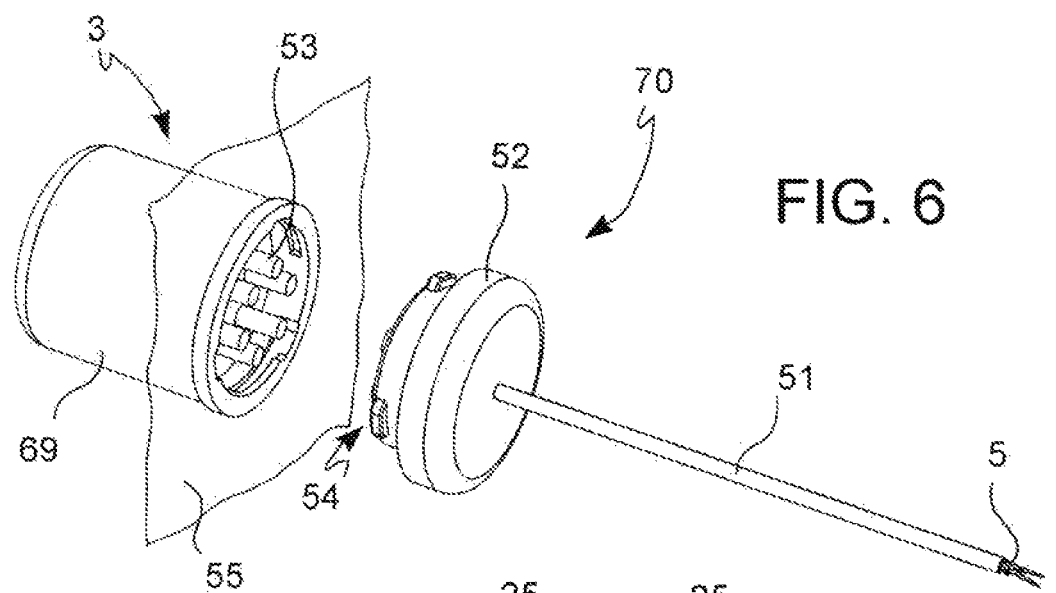
FIG. 6 is a perspective view of a portion of a slave manipulator disconnected from a surgical instrument, according to an embodiment.
Figure 7:
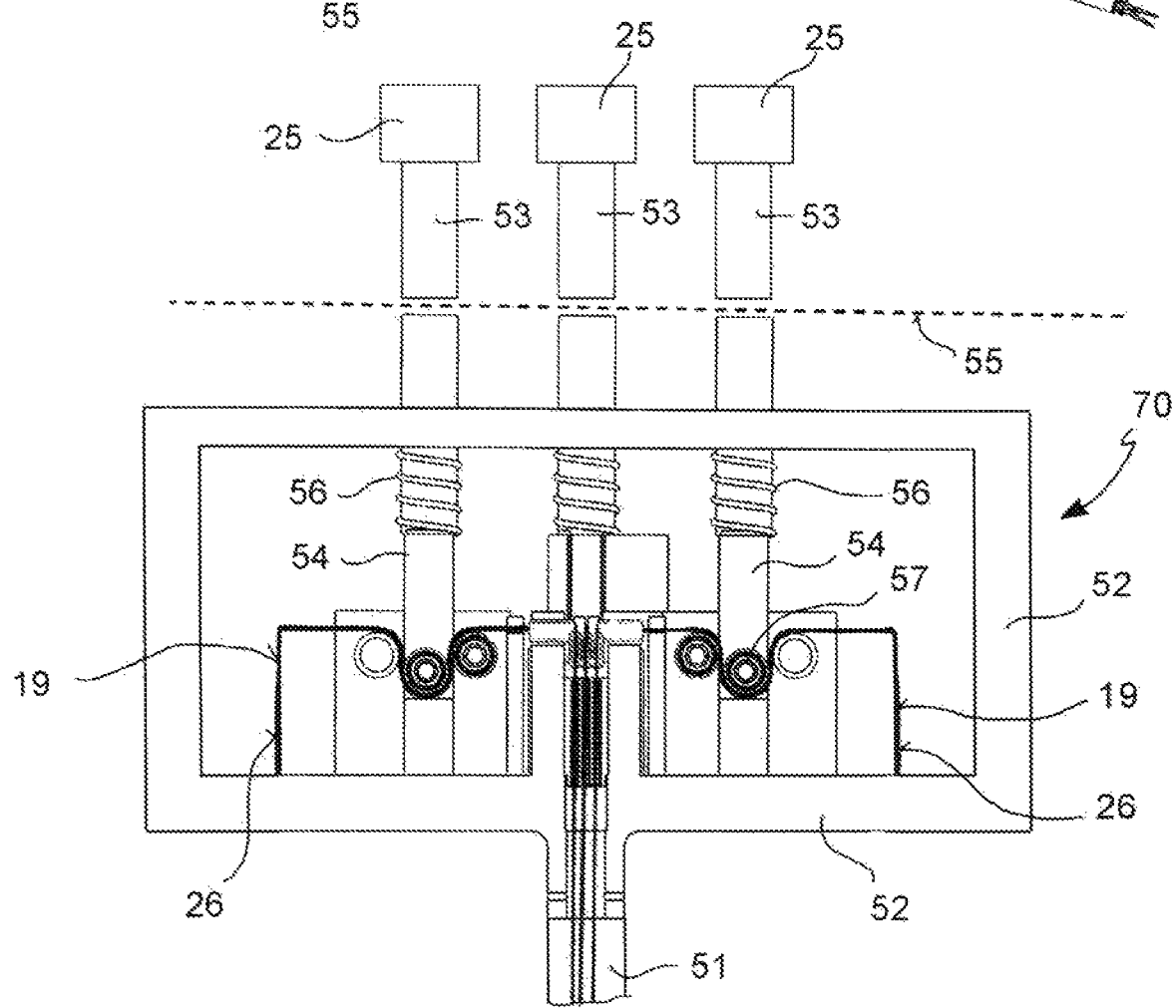
FIG. 7 is a sketch depicting a cross-section of a portion of a slave manipulator and a surgical instrument, according to an embodiment.
Figure 8:
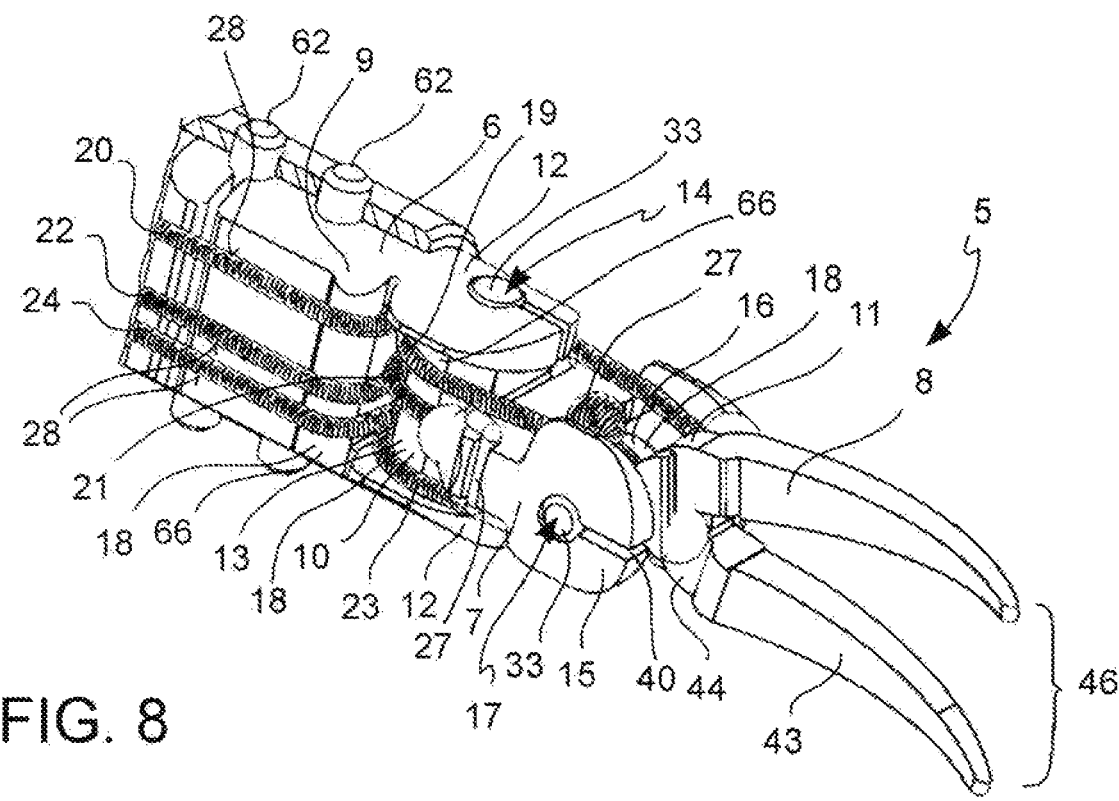
FIG. 8 is a perspective view of a jointed subassembly, according to an embodiment, wherein some parts are sectioned for sought of clarity.
Figure 9:
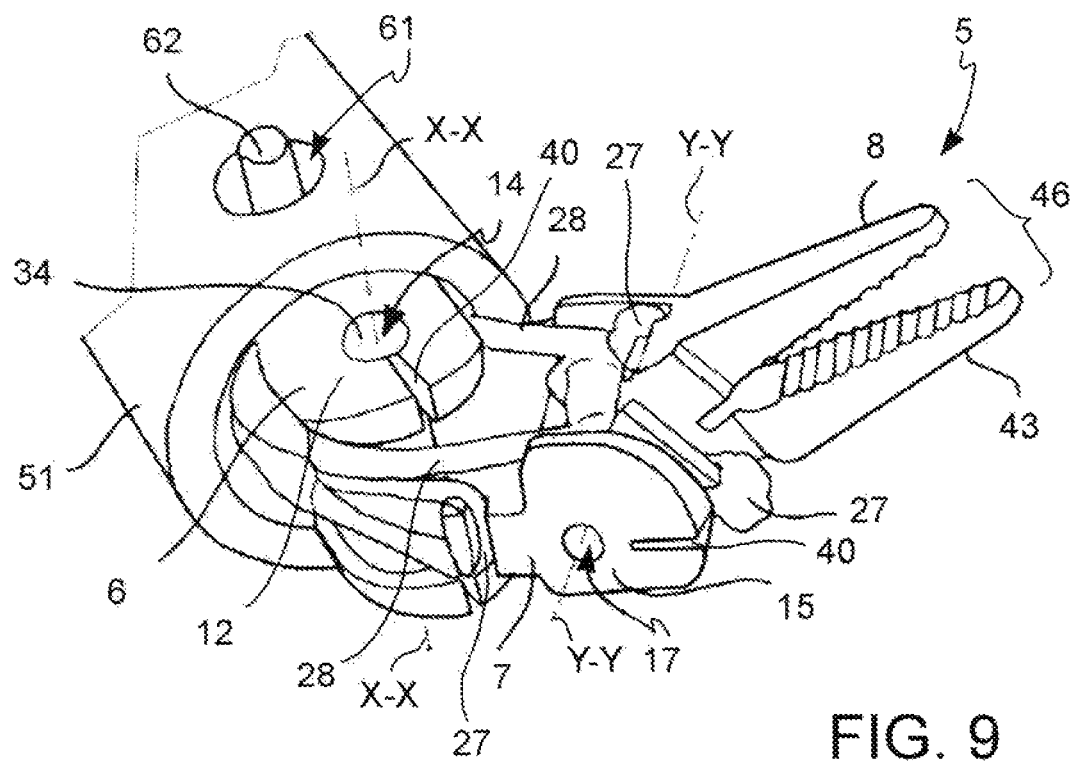
FIG. 9 is a perspective view of a jointed subassembly, according to an embodiment.
Figure 10:
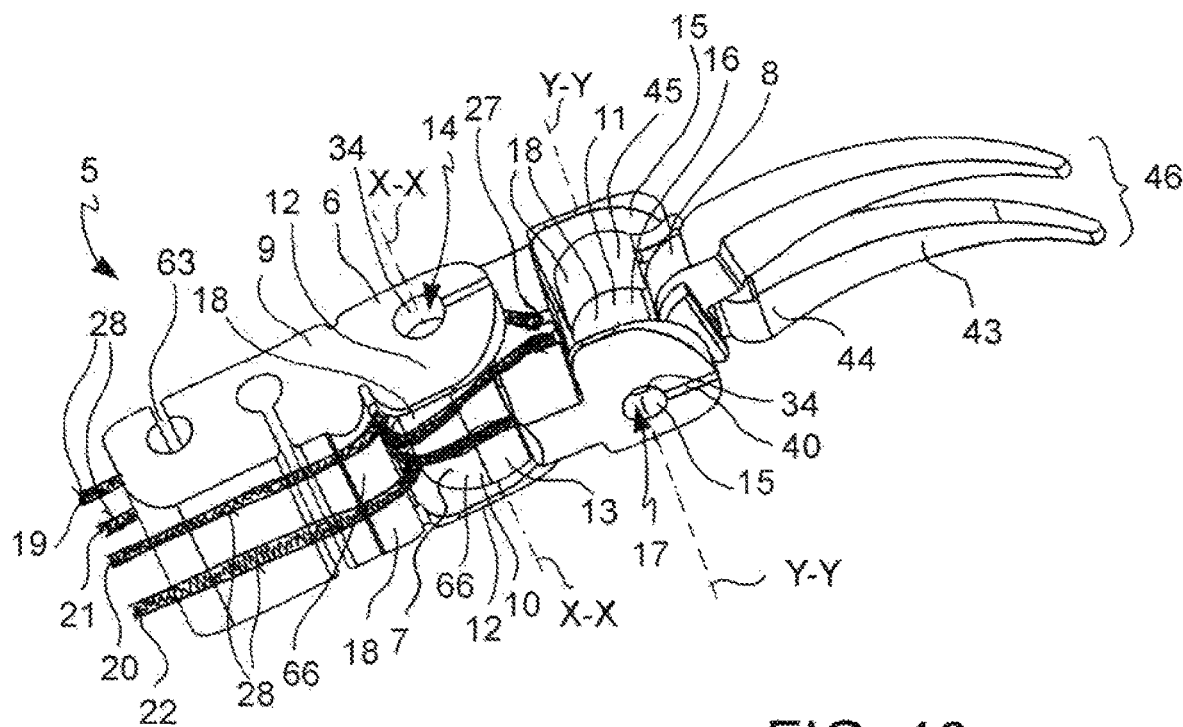
FIG. 10 is a perspective view of a jointed subassembly, according to an embodiment.
Figure 11:
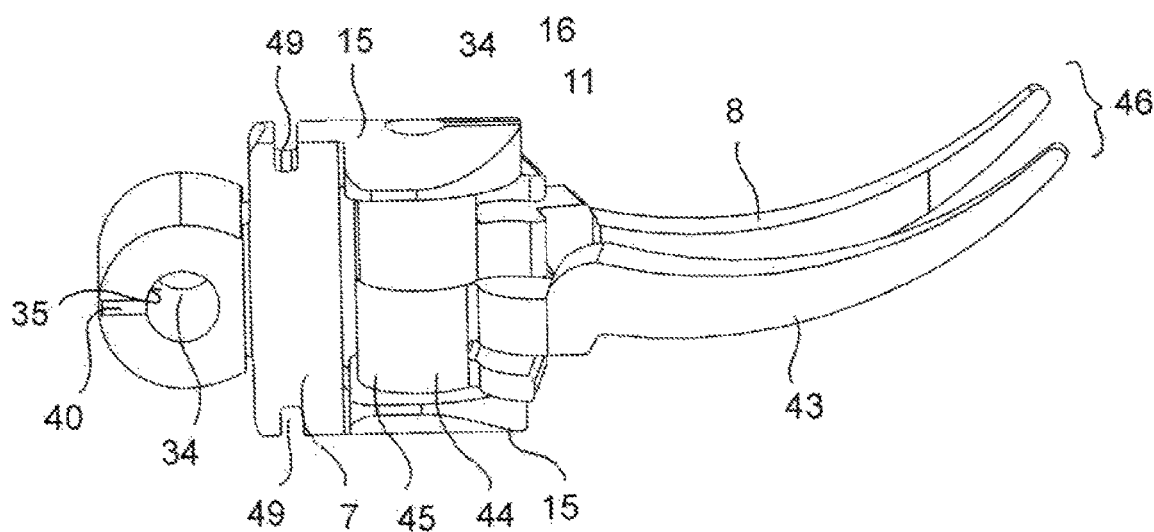
FIG. 11 is a perspective view of a portion of a jointed subassembly, according to an embodiment.
Figure 12:
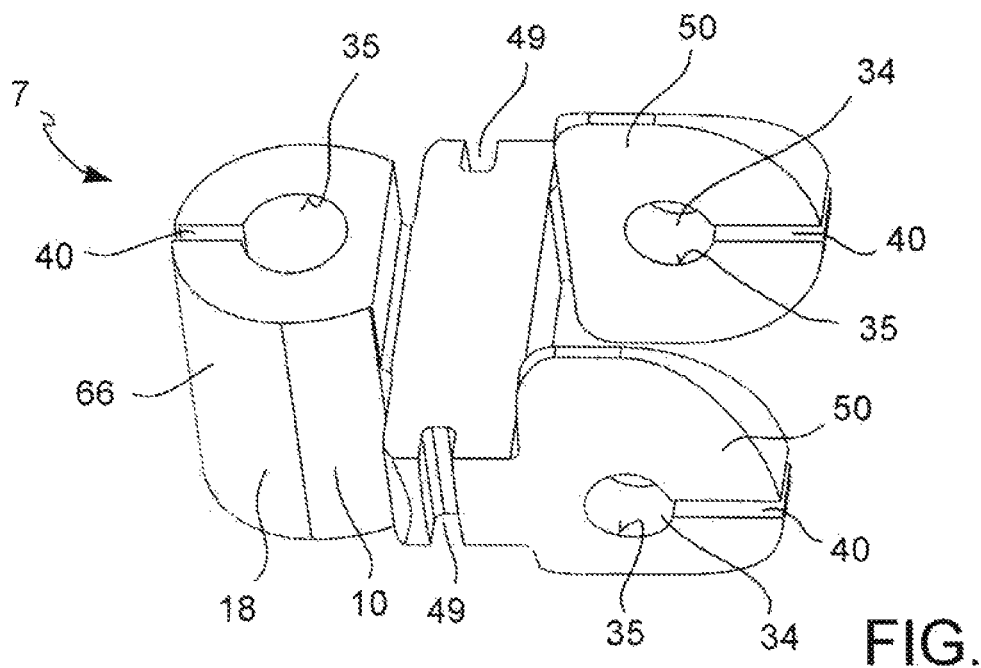
FIG. 12 is a perspective view of a link, according to an embodiment.
Figure 13A:
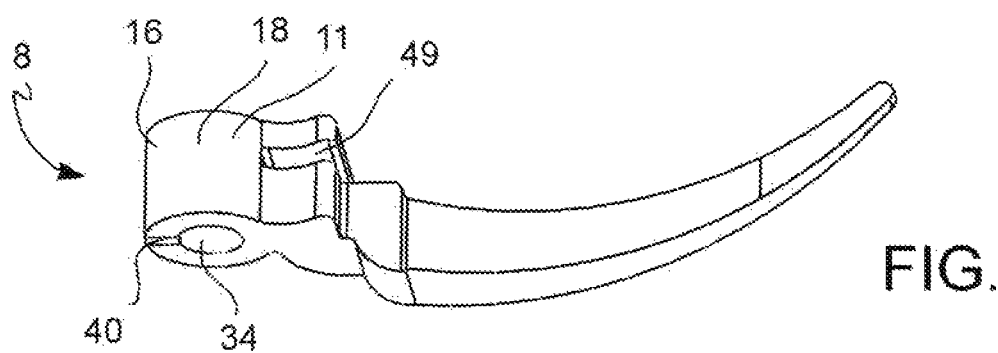
FIG. 13A is a perspective view of a link, according to an embodiment.
Figure 13B:
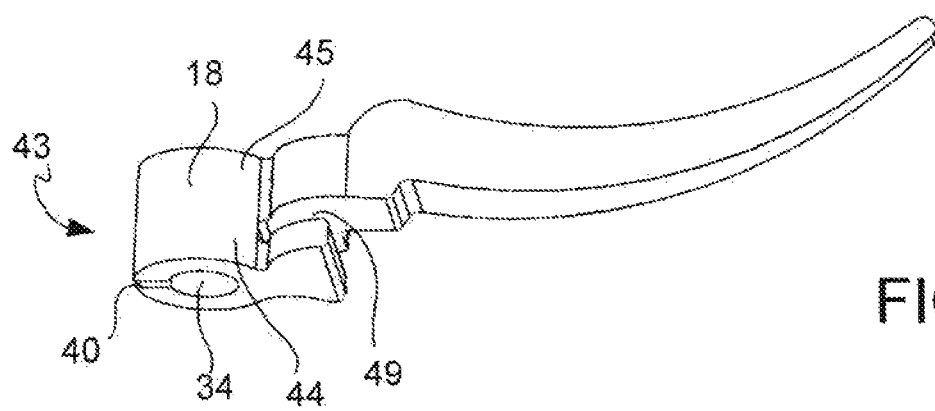
FIG. 13B is a perspective view of a link, according to an embodiment.
Figure 14:
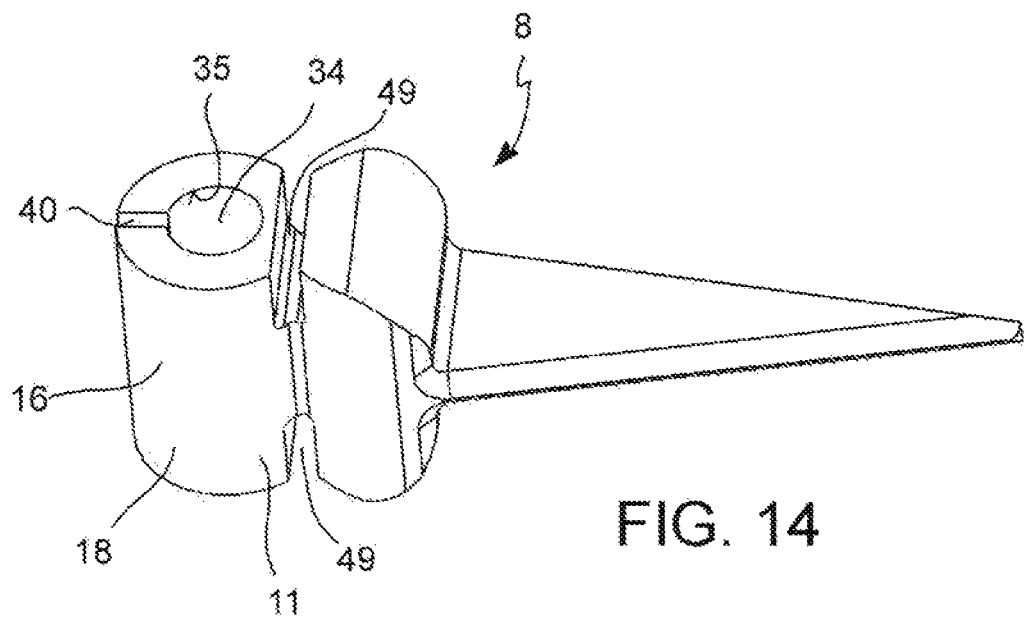
FIG. 14 is a perspective view of a link, according to an embodiment.
Figure 15:
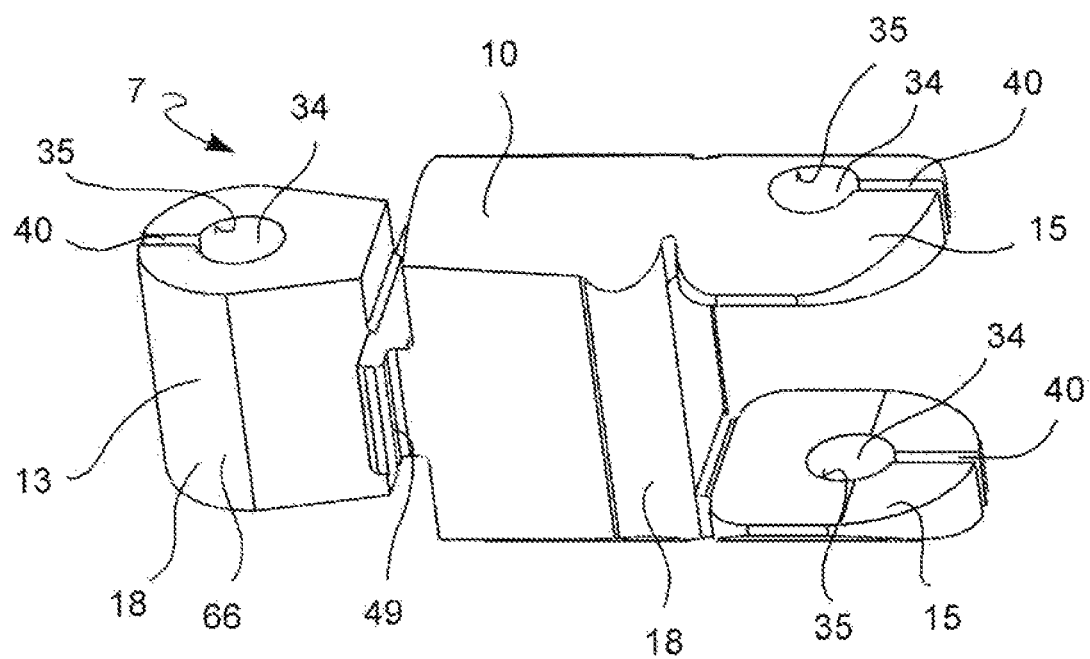
FIG. 15 is a perspective view of a link, according to an embodiment.
Figure 16:
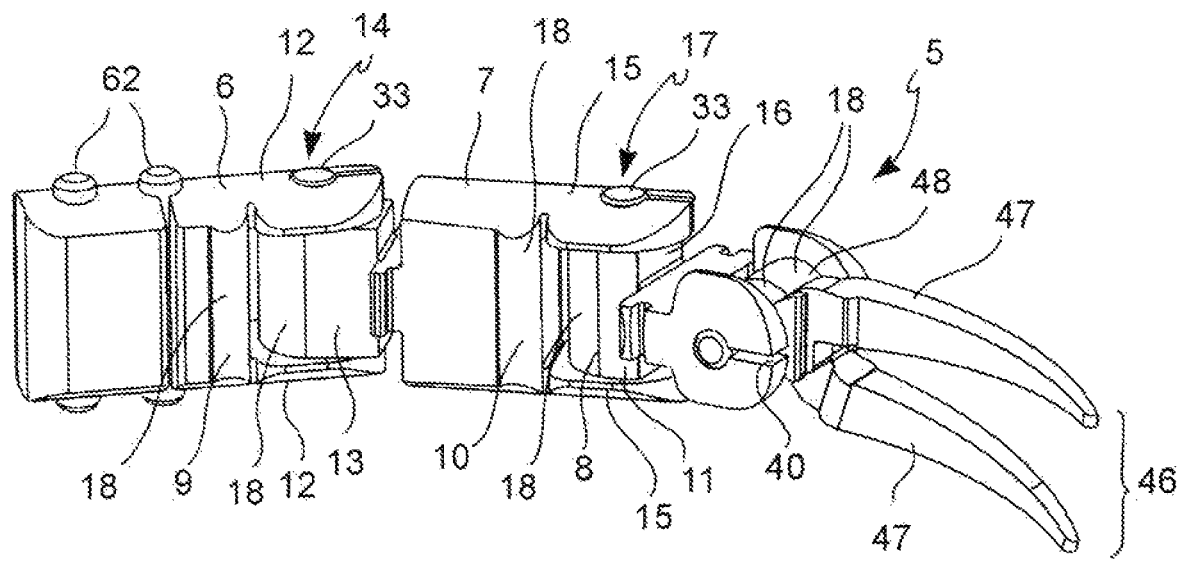
FIG. 16 is a perspective view of a jointed subassembly, according to an embodiment, wherein the tendons are not shown.
Figure 17:
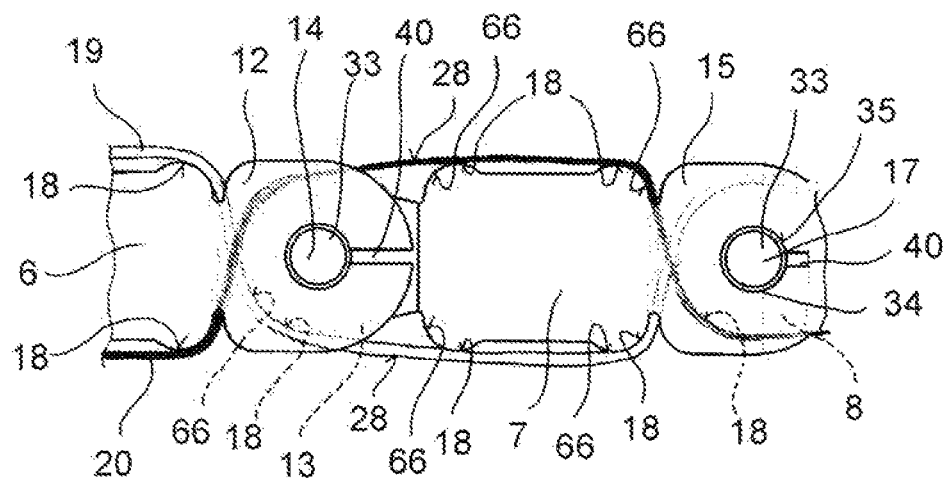
FIG. 17 is a sketch in plane view of a portion of a jointed subassembly, according to an embodiment, wherein tendons are shown.
Figure 18:
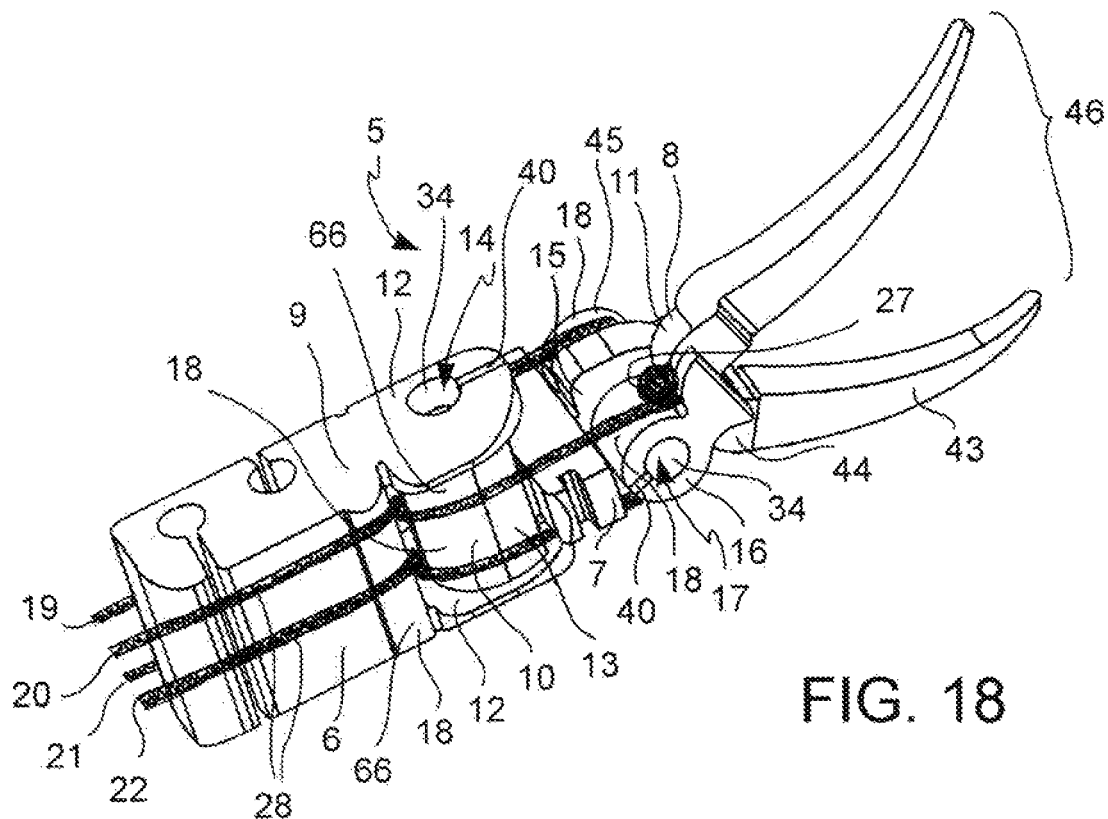
FIG. 18 is a perspective view of a jointed subassembly, according to an embodiment.

According to a general embodiment, a robotic microsurgery assembly 1 comprises at least one master tool 2, suitable to detect a manual command, at least one slave manipulator 3 and at least a surgical instrument 70, and at least one control unit 4 configured to receive at least a first command signal 59 comprising information about said manual command and to send a second command signal 60 to at least one actuator 25 in said slave manipulator 3 to control said surgical instrument 70.

According to an embodiment, said surgical instrument 70 is a slave surgical instrument 70. According to an embodiment, said surgical instrument 70 is a medical instrument 70.

According to an embodiment, said control unit 4 is connected to an actuator drive unit 58, suitable for send said second command signal to said at least one actuator 25. According to an embodiment, said at least one control unit 4 comprises a CPU. According to an embodiment, said at least one control unit 4 comprises at least one processor unit. According to an embodiment, said at least one control unit 4 provides a feedback control circuit based on the information acquired by a detection system suitable for detecting the action, for example the displacement provided and/or the force exerted by, of said at least one actuator 25. According to an embodiment, said master tool 2 is designed to be handled by a surgeon 30. According to an embodiment, at least a portion of said surgical instrument 70 is designed to operate on the anatomy of a patient 29.

Said surgical instrument 70 comprises at least one jointed subassembly 5.

According to an embodiment, the term "jointed subassembly" refers to a serial sequence of links connected one to the next by joints suitable to support and/or orient and/or position and/or influence the position of an end effector of said surgical instrument 70. According to an embodiment, from a functional point of view, said jointed subassembly can be a wrist joint, an elbow joint or a shoulder joint of a robotic or mechatronic structure.

Said jointed subassembly 5 comprises links.

According to a preferred embodiment, said jointed subassembly 5 comprises at least a first link 6, a second link 7, and a third link 8. In this way, said jointed subassembly 5 comprises at least three links 6, 7, 8.

Said first link 6 is formed of a first link structural body 9, said first link structural body 9 being in a single piece.

According to a preferred embodiment, the terminology "single piece" indicates that any degree of freedom is avoided within a single link structural body, when in operative conditions. According to an embodiment, the terminology "single piece" indicates that a link structural body can comprise two or more pieces joined together in such way to avoid any degree of freedom within a single link structural body.

According to an embodiment, the terminology "single piece" indicates also that a link structural body can comprise two or more pieces joined together in such way that the relative spatial orientation of said two or more pieces is rigidly locked, when in operative conditions.

According to an embodiment, the terminology "single piece" indicates also that a link structural body is 10 onobloc.

According to an embodiment, Said second link 7 is formed of a second link structural body 10, said second link structural body 10 being in a single piece.

According to an embodiment, Said third link 8 is formed of a third link structural body 11, said third link structural body 11 being in a single piece.

According to an embodiment, each link is formed of a link structural body.

Said first link structural body 9 comprises a first link distal portion 12 forming a first joint proximal portion, and said second link structural body 10 comprises a second link proximal portion 13 forming a first joint distal portion. According to an embodiment, said first link distal portion 12 of said first link structural body 9 comprises two clevis prongs, in such way to be suitable to form a clevis joint. According to an embodiment, said second link proximal portion 13 comprises two clevis prongs, in such way to be suitable to form a clevis joint.

Said first link distal portion 12 and said second link proximal portion 13 cooperate to form at least partially a first joint 14 providing a single degree of freedom between said first link 6 and said second link 7. According to a preferred embodiment, said single degree of freedom between said first link 6 and said second link 7 is a roto-translational degree of freedom around a first joint axis X-X, and preferably, said roto-translational degree of freedom is a rotational degree of freedom around said first joint axis X-X.

Said second link structural body 10 further comprises a second link distal portion 15 forming a second joint proximal portion, and said third link structural body 11 comprises a third link proximal portion 16 forming a second joint distal portion. According to an embodiment, said second link distal portion 15 comprises two clevis prongs, in such way to be suitable to form a clevis joint. According to an embodiment, said third link proximal portion 16 comprises two clevis prongs, in such way to be suitable to form a clevis joint.

Said second link distal portion 15 and said third link proximal portion 16 cooperate to form at least partially a second joint 17 providing a single degree of freedom between said second link 7 and said third link 8. According to a preferred embodiment, said single degree of freedom between said second link 7 and said third link 8 is a roto-translational degree of freedom around a second joint axis Y-Y, and preferably said roto-translational degree of freedom is a rotational degree of freedom around said second joint axis Y-Y.

According to an embodiment, said first joint 14 and said second joint 17 are each suitable for providing a single degree of freedom.

According to an embodiment, said first joint 14 is suitable for locking the relative movement between said first link 6 and said second link 7 in all directions except for a relative rotation around a first joint axis X-X. According to an embodiment, said second joint 17 is suitable for locking the relative movement between said second link 7 and said third link 8 in all directions except for a relative rotation around a second joint axis Y-Y.

According to an embodiment, said first link structural body 9, said second link structural body 10 and said third link structural body 11 form a kinematic chain. According to an embodiment, said first link structural body 9, said second link structural body 10 and said third link structural body 11 are directly connected in series to form a kinematic chain According to an embodiment, said first link 6 is an adjacent link in respect of said second link 7, with no intervening links in the kinematic chain. According to an embodiment, said second link 7 is an adjacent link in respect of both said first link 6 and said third link 8. According to an embodiment, said third link 8 is an adjacent link in respect of said second link 7. According to an embodiment, said first link structural body 9 is an adjacent link structural body in respect of said second link structural body 10. According to an embodiment, said second link structural body 10 is an adjacent link structural body in respect of both said first link structural body 9 and said third link structural body 11. According to an embodiment, said third link structural body 11 is an adjacent link structural body in respect of said second link structural body 10.

According to an embodiment, said kinematic chain can comprises two or more branches of kinematic chain. According to an embodiment, said two or more branches extend from a single joint, for example from said second joint 17. According to an embodiment, said two or more branches of kinematic chain share at least one link. According to an embodiment, said two or more branches of kinematic chain share at least two links out of three links of the jointed subassembly.

According to an embodiment, each of said first joint 14 and said second joint 17 refer to mechanical means adapted to provide a link in the kinematic chain with a rotational degree of freedom around a joint axis with respect to an adjacent link in the kinematic chain. According to an embodiment, each of said joint axis X-X, Y-Y is a common joint axis shared by two adjacent links, such that the two adjacent links can rotate one with respect to the other around said common joint axis. According to an embodiment, said first joint 14 defines a first joint axis X-X, wherein said first joint axis X-X is a common joint axis shared by both said first link 6 and said second link 7, such that the two adjacent links can rotate one with respect to the other around said common joint axis. According to an embodiment, said second joint 17 defines a second joint axis Y-Y, wherein said second joint axis Y-Y is a common joint axis shared by both said second link 7 and said third link 8, such that the two adjacent links can rotate one with respect to the other around said common joint axis According to an embodiment, a kinematic chain formed by said at least three links 6, 7, 8 have two degrees of freedom.

According to an embodiment, a kinematic chain formed by said at least three links 6, 7, 8 have exactly two degrees of freedom. In other words, according to an embodiment, the total number of degrees of freedom of a kinematic chain formed by said at least three links 6, 7, 8 is two. According to an embodiment, a kinematic chain formed by said first link 6, said second link 7 and said third link 8 have exactly two degrees of freedom. In other words, according to an embodiment, the total number of degrees of freedom of a kinematic chain formed by said first link 6, said second link 7 and said third link 8 is two.

According to an embodiment, said jointed subassembly 5 avoids to comprise actuators. According to an embodiment, said jointed subassembly 5 avoids to comprise actuators within said kinematic chain. According to an embodiment, no actuators are provided among said links.

At least two among said first link structural body 9, said second link structural body 10 and said third link structural body 11 comprise at least one tendon contact surface 18, avoiding that said at least one tendon contact surface 18 is a hole surface. In other words, said at least one tendon contact surface 18 avoids to delimit a through hole in a link structural body 9 or 10 or 11. According to an embodiment, a normal line, or orthogonal line, to said at least one tendon contact surface 18 avoids to intersect the structural body comprising said at least one tendon contact surface 18. According to an embodiment, said tendon contact surface 18 avoids to face itself. According to an embodiment, said tendon contact surface 18 urges said tendon intermediate portion 28 away from the link structural body comprising said tendon contact surface 18.

According to an embodiment, said tendon contact surface 18 embraces one of said tendon over an angle equal to or lower than 180 degrees. According to an embodiment, said tendon contact surface 18 is an outer surface of one of said link structural bodies 9, 10, 11. According to an embodiment, said tendon contact surface 18 delimits at least partially the encumber of one of said link structural bodies 9, 10, 11. According to an embodiment, each tendon comprises a first longitudinal side and a second opposite longitudinal side, wherein one between said first longitudinal side and said second longitudinal side is in contact with at least one of said links. In other words, when said first longitudinal side is in contact with a given link, said first longitudinal side faces away from said given link. According to an embodiment, each of said first longitudinal side and said second opposite longitudinal side covers on said tendon an angle of substantially 180 while remaining disjointed one another.

Said surgical instrument 70 comprises tendons 19, 20, 21, 22, 23, 24, 31, 32. According to an embodiment, said tendons acts as actuation cables suitable for working only in traction.

Said surgical instrument 70 comprises at least three tendons. According to an embodiment, each tendon of said at least three tendons comprises a tendon proximal portion 26, associated to said at least one actuator 25, a tendon distal portion 27, secured to and extending over said second link 7 or to said third link 8, a tendon intermediate portion 28, extending between said tendon proximal portion 26 and said tendon distal portion 27. According to an embodiment, said tendon distal portion 27 of each tendon 19 wraps around a portion of the link to which is secured thereto, avoiding to slide over the link to which is secured thereto.

According to an embodiment, said surgical instrument 70 comprises a further tendon so as to comprise at least four tendons, wherein said at least one intermediate portion 28 of each of said at least four tendons contacts said jointed subassembly 5 only in said at least one tendon contact surface 18.

According to an embodiment, a pair of tendons have their tendon distal portions 27 secured to a same link, so as to work as. In other words, a pair of tendons are secured to a same link so as to work as antagonist tendons. According to an embodiment, a pair of tendons share their tendon distal portions 27, so as to work as antagonist tendons. According to an embodiment, a pair of tendons working as antagonist tendons are in single piece. According to an embodiment, said tendons 19, 20, 21, 22, 23, 24, 31, 32 comprises a first pair of tendons 19, 20, suitable to work as antagonist tendons. According to an embodiment, said tendons 19, 20, 21, 22, 23, 24, 31, 32 comprises a second pair of tendons 21, 22, suitable to work as antagonist tendons.

According to an embodiment, a pair of tendons have their tendon distal portions 27 secured to a same link, so as to work as one tendon. In other words, a pair of tendons are secured to a same link so as to work in parallel as a single tendon. According to an embodiment, a pair of tendons share their tendon distal portions 27, so as to work in parallel as a single tendon. According to an embodiment, a pair of tendons working as a single tendon are in single piece. According to an embodiment, said tendons 19, 20, 21, 22, 23, 24, 31, 32 comprises a first pair of tendons 19, 20, suitable to work as a single tendon. According to an embodiment, said tendons 19, 20, 21, 22, 23, 24, 31, 32 comprises a second pair of tendons 21, 22, suitable to work as a single tendon. According to an embodiment, said tendons 19, 20, 21, 22, 23, 24, 31, 32 comprises a third pair of tendons 23, 24, suitable to work as antagonist tendons. According to an embodiment, said tendons 19, 20, 21, 22, 23, 24, 31, 32 comprises a fourth pair of tendons 31, 32 suitable to work as antagonist tendons.

Figure 35:
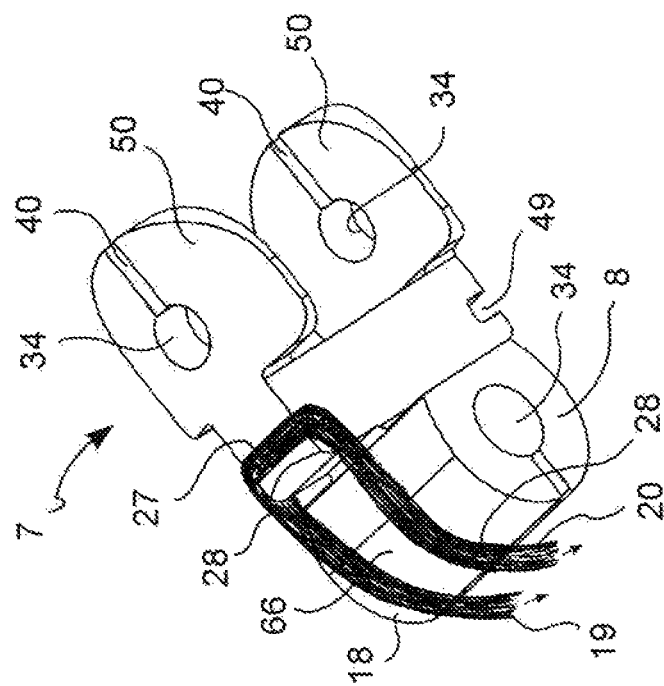
FIG. 35 is a perspective view of a link, according to an embodiment.
Figure 34:
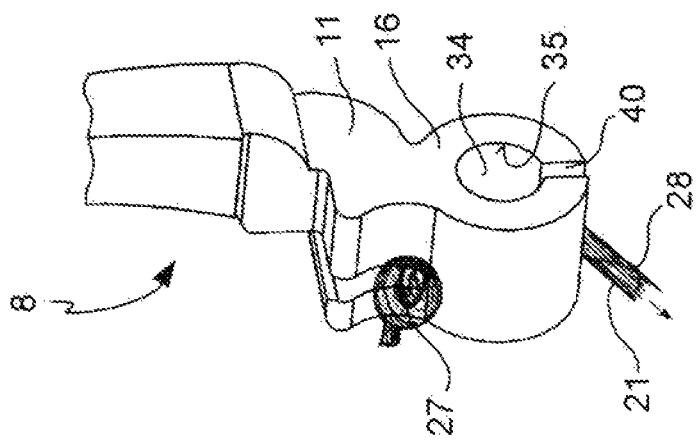
FIG. 34 is a perspective view of the link and the tendon shown in FIG. 33, depicted from the point of view indicated by the arrow XXXIV of FIG. 33.
Figure 33:
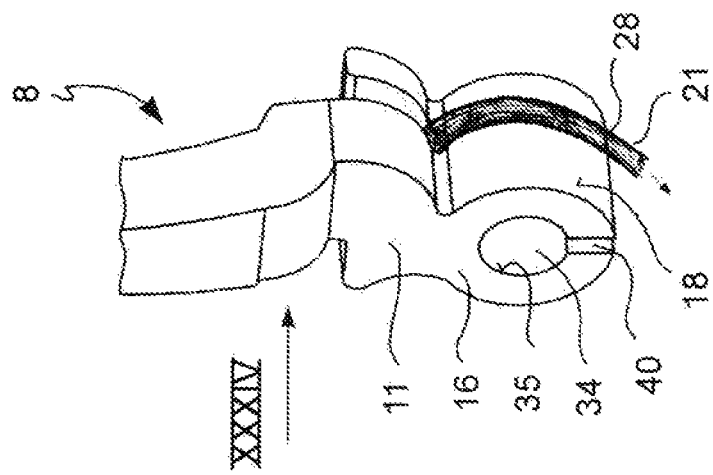
FIG. 33 is a perspective view of a link and a portion of a tendon, according to an embodiment.
Figure 36:
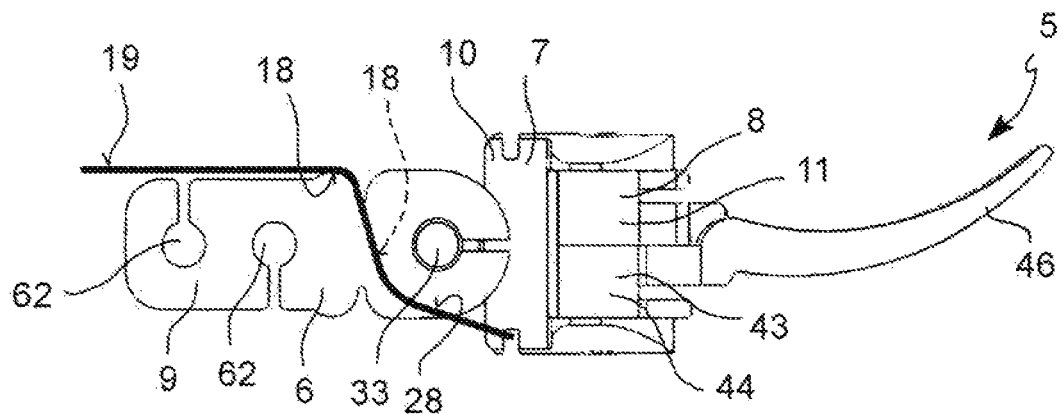
FIGS. 36 and 37 are plane views showing a jointed subassembly having transparent parts for sought of clarity and at least one tendon, according to some embodiments.
Figure 37:
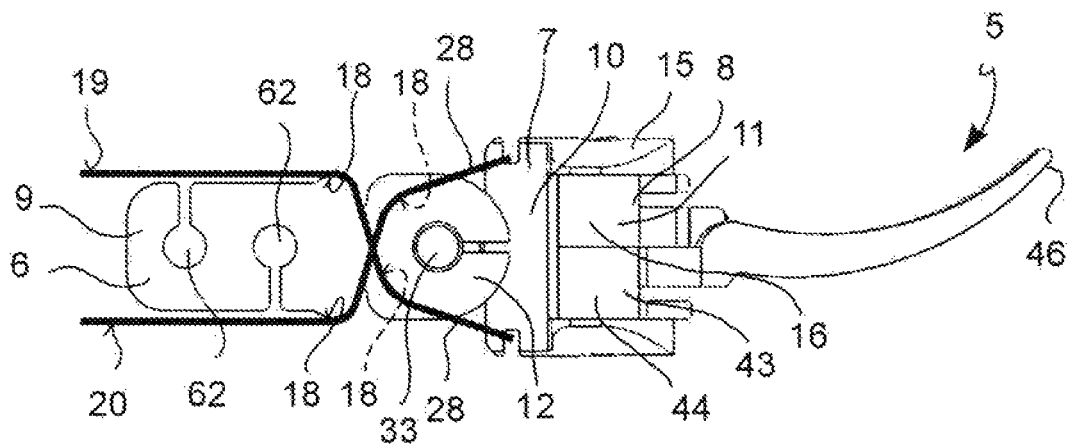
Figure 38:
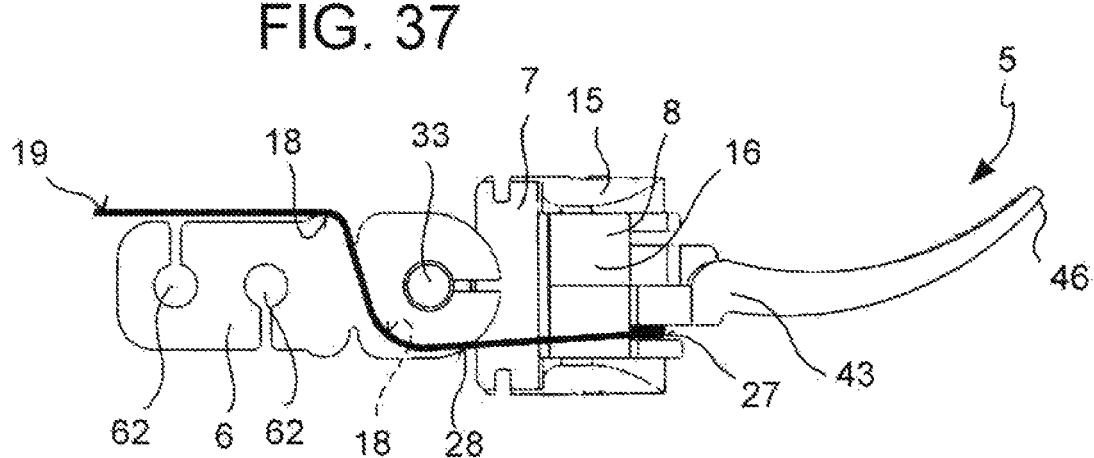
FIGS. 38 and 39 are plane views showing a jointed subassembly having transparent parts for sought of clarity and a tendon, according to some embodiments.
Figure 39:
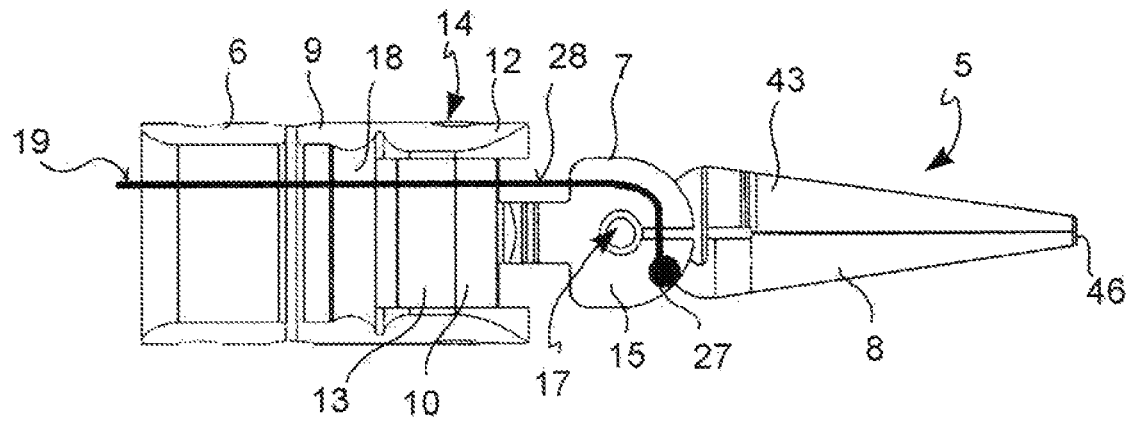
Figure 40:
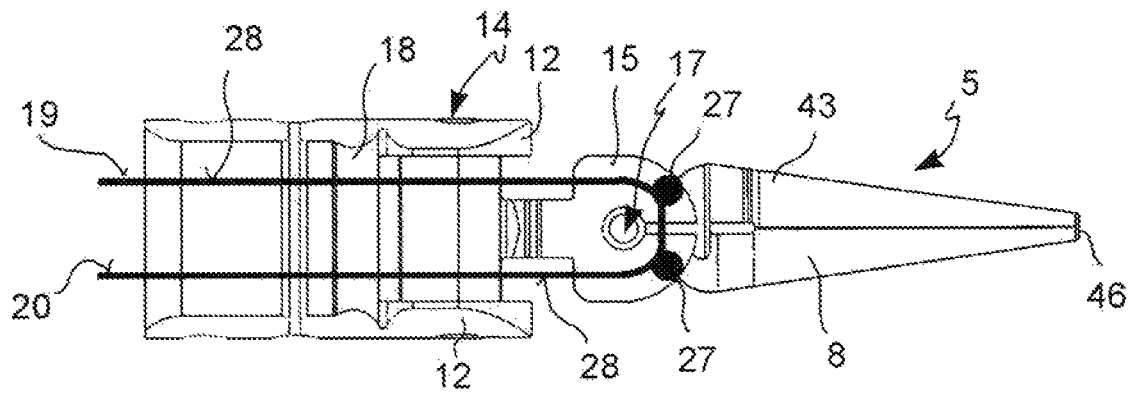
FIGS. 40 and 41 are plane views showing a jointed subassembly having transparent parts for sought of clarity and at least one tendon, according to some embodiments.
Figure 41:
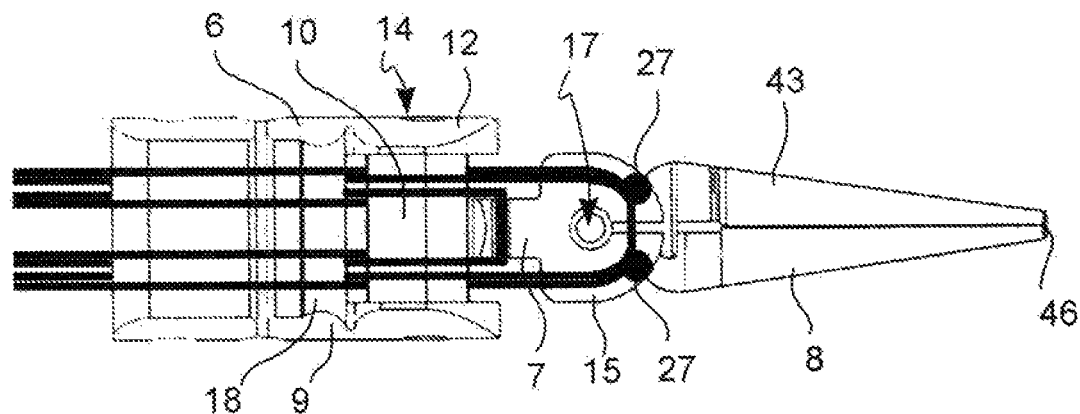
Figure 42:
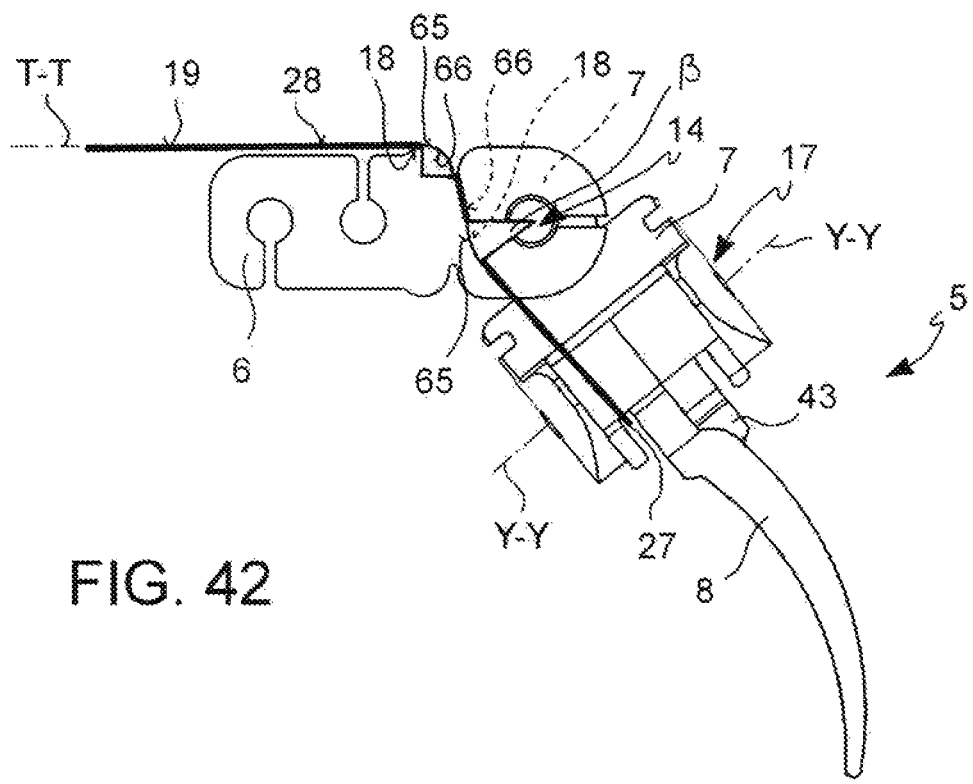
FIG. 42 is a sketch in plane view showing a configuration of a jointed subassembly, according to an embodiment, wherein a tendon describes a total winding angle.
Figure 43:
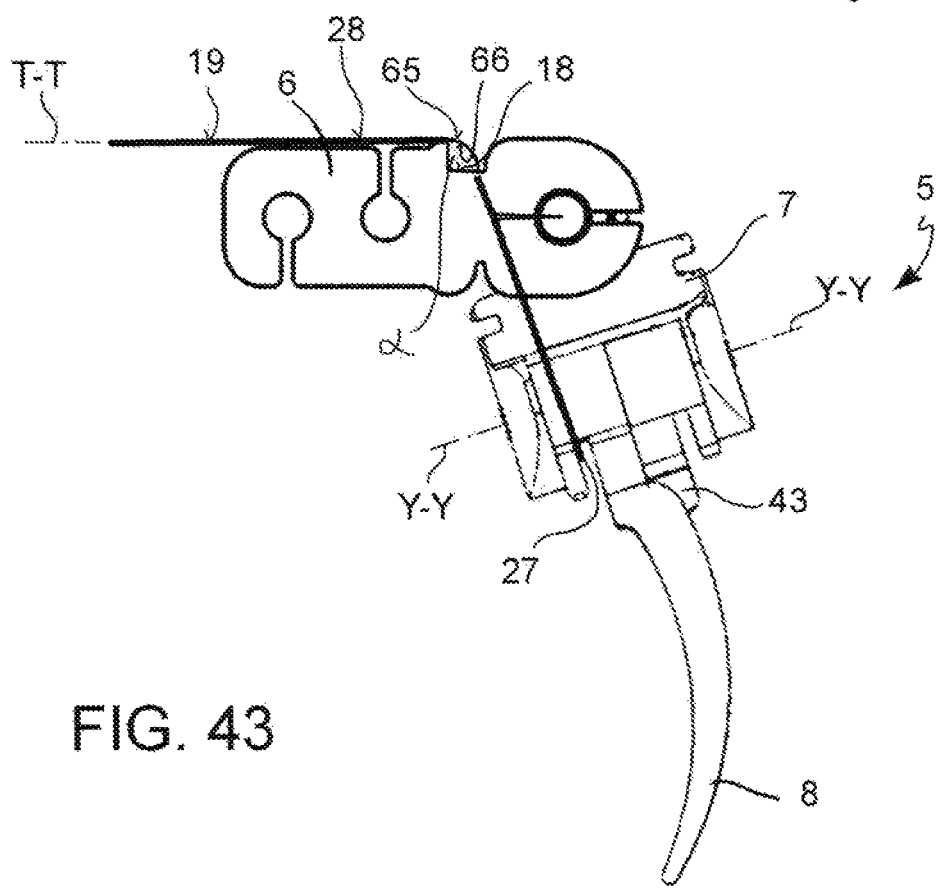
FIG. 43 is a sketch in plane view showing a configuration of a jointed subassembly, according to an embodiment, wherein a tendon describes a total winding angle.
Figure 44:
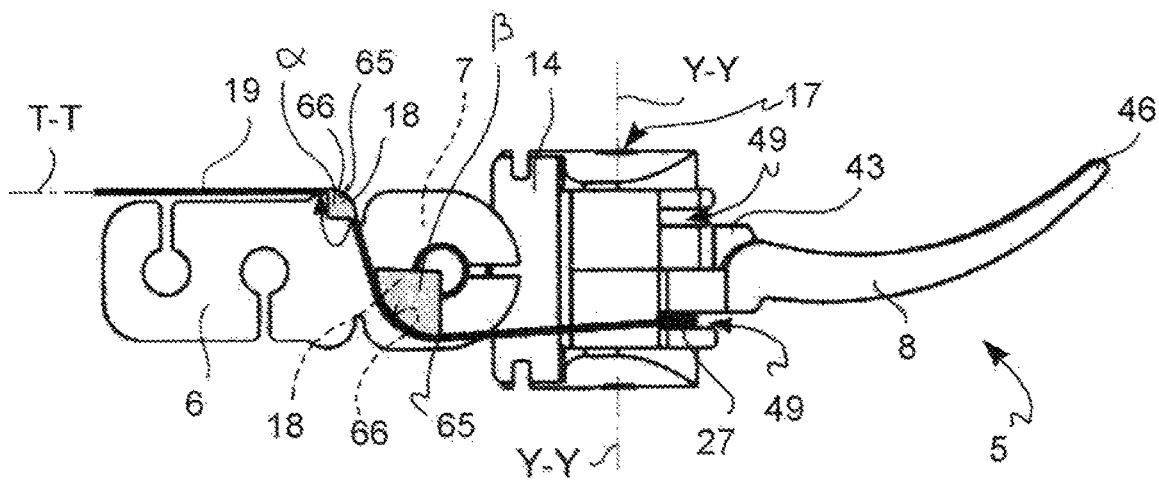
FIG. 44 is a sketch in plane view showing a configuration of a jointed subassembly, according to an embodiment, wherein a tendon describes a total winding angle.
Figure 45:
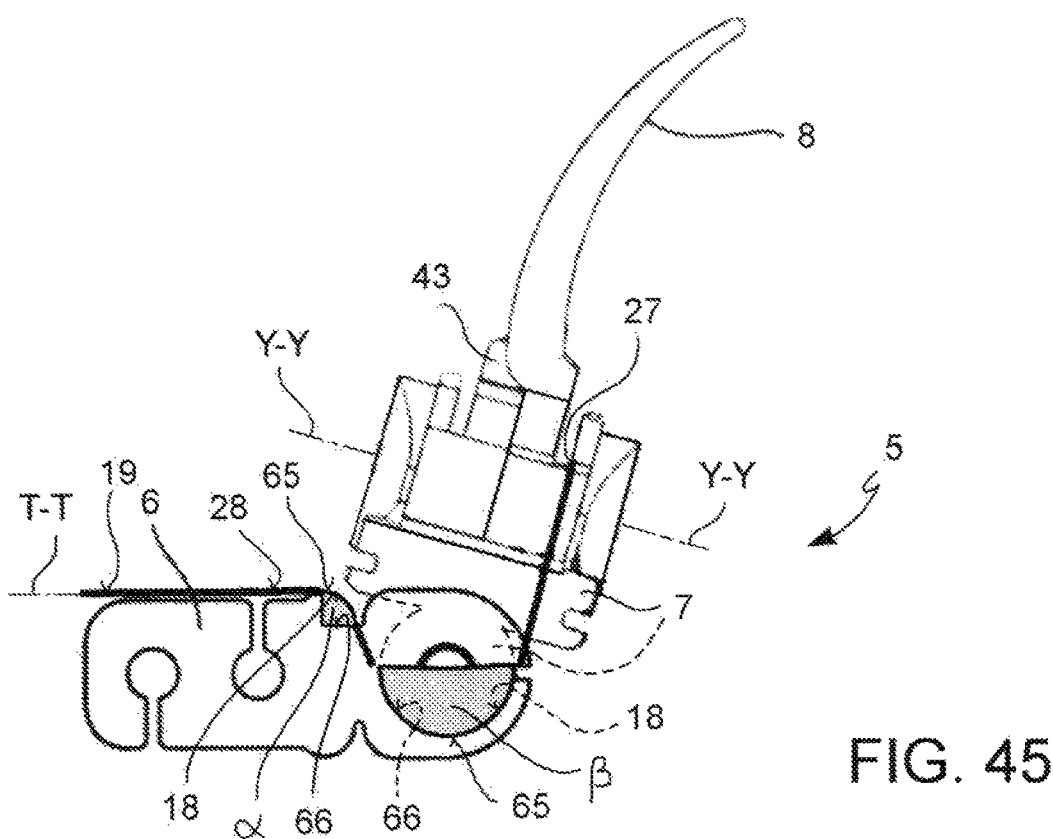
FIG. 45 is a sketch in plane view showing a configuration of a jointed subassembly, according to an embodiment, wherein a tendon describes a total winding angle.
Figure 46:
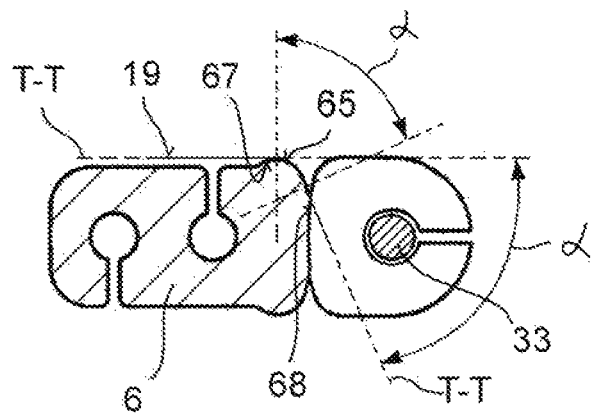
FIG. 46 is a sketch showing a cross-section of a link, according to an embodiment, wherein a tendon describes a local winding angle.
Figure 47:
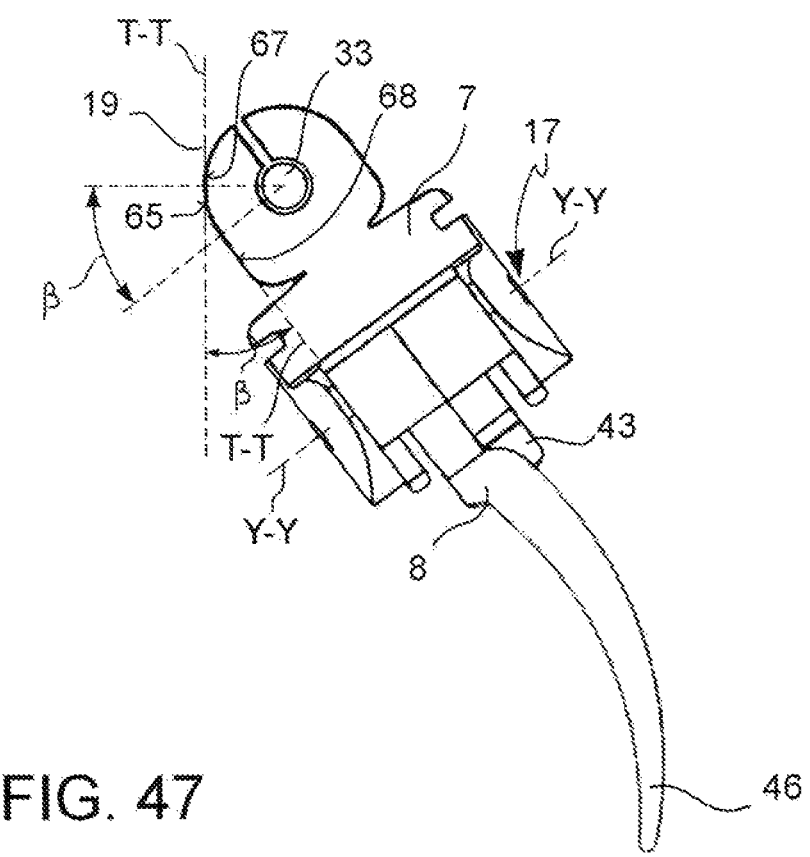
FIG. 47 is a sketch showing a cross-section of a link, according to an embodiment, wherein a tendon describes a local winding angle.

According to an embodiment, at least one between said second link 7 and to said third link 8 comprises at least a tendon securing portion 49, suitable to receive said tendon distal portion 27. According to an embodiment, at least one between said second link 7 and to said third link 8 comprises two tendon securing portions 49, suitable to receive said tendon distal portion 27 of two tendons working as antagonist tendons. For example, as shown in FIG. 35, said tendons 19 and 20 works in parallel as a single tendon.

According to a preferred embodiment, said tendon intermediate portion 28 of at least two of said tendons, and preferably of each tendon of said tendons, contacts said jointed subassembly 5 exclusively in said at least one tendon contact surface 18 of at least two among said first link structural body 9, said second link structural body 10 and said third link structural body 11.

Preferably, said said tendon intermediate portion 28 of at least two of said tendons contacts said jointed subassembly 5 exclusively in at least one tendon contact surface 18 of said first link structural body 9 and in at least one tendon contact surface 18 of said second link structural body 10, wherein said first link structural body 9 and said second link structural body 10 comprise said at least one tendon contact surface 18, avoiding that said at least one tendon contact surface is a hole surface.

This avoids the need of any additional parts for routing the tendons and minimizes parts count and difficulty of assembly. Further, that allows to avoid to provide internal moving part in the links. This also avoids unnecessary friction and wear of tendons from further contact with the jointed assembly.

According to a preferred embodiment, this avoids that said tendon intermediate portion 28 of each tendon contacts any other portions of said jointed subassembly 5. According to an embodiment, said tendon intermediate portion 28 of each tendon contacts said jointed subassembly only in said at least one tendon contact surface 18.

Advantageously, thanks to the characteristics of surgical instrument 70, it is possible to miniaturize the dimensions of said jointed subassembly 5.

According to an embodiment, each of said first link structural body 9, said second link structural body 10 and said third link structural body 11 comprise at least one tendon contact surface 18.

According to an embodiment, said at least one tendon contact surface 18 is a groove surface.

According to an embodiment, at least one link structural body of said link structural bodies can be associated to appendices in separate pieces with respect of said link structural body, such as pulleys, for example idle pulleys, but said appendices avoid to provide a contact surface for any one of said tendon intermediate portions 28.

According to an embodiment, said first link distal portion 12 and said second link proximal portion 13 cooperate in a geometric coupling, to form said first joint 14. According to an embodiment, said second link distal portion 15 and said a third link proximal portion 16 cooperate in a geometric coupling, to form said second joint 17.

According to an embodiment, at least one between said first joint 14 and said second joint 17 is a pivot joint. According to an embodiment, said pivot joint is a rotational joint which provides a mechanical pivot for the joint axis X-X or Y-Y.

According to an embodiment, at least one between said first joint 14 and said second joint 17 is a rolling joint. According to one embodiment, said rolling joint provides a rolling contact between a link structural body of a link and a link structural body of an adjacent link, over respective rolling surfaces such that the rolling motions happens around a fixed joint axis X-X or Y-Y.

According to an embodiment, at least one between said first joint 14 and said second joint 17 is a pin joint.

According to an embodiment, said pin joint comprises at least one pin 33 and at least one pin seat 34, suitable to receive said at least one pin 33. According to an embodiment, said pin 33 as a prevailing longitudinal development.

According to an embodiment, said at least one pin 33 is of smaller diameter that said at least one pin seat 34 receiving said at least one pin 33, so that a clearance results in the coupling of said pin 33 and said pin seat 34.

According to an embodiment, said pin seat 34 is a pass-through hole, delimited by at least one of said link structural bodies 9, 10, 11.

According to an embodiment, said pin seat 34 is a cavity, delimited by at least one of said link structural bodies 9, 10, 11.

According to an embodiment, said pin seat 34 is a cavity, having a cavity mouth 40 narrower than said at least one pin 33 and said cavity mouth 40 is unsuitable for receiving said pin 33. Such a cavity prevents the pin 33 from exiting the pin seat 34 in a direction transversal to the longitudinal development of said pin 33.

According to an embodiment, said pin seat 34 is delimited by a pin seat boundary 35 facing said pin seat 34. Preferably, said pin seat boundary 35 is suitable for facing a pin 33 received in said pin seat 34.

According to an embodiment at least one among said first link distal portion 12 of said first link structural body 9, said second link proximal portion 13 of said second link structural body 10, said second link distal portion 15 of said second link structural body 10, and said third link proximal portion 16 of said third link structural body 11, comprises said pin seat boundary 35 which delimits said pin seat 34 for receiving a pin 33.

According to an embodiment, said pin seat boundary 35 is substantially circular. According to an embodiment, said pin seat boundary 35 comprises an arch of a circumference. According to an embodiment, said pin seat boundary 35 describes a paraboloid profile. According to an embodiment, said pin seat boundary 35 describes a cam profile, suitable for cooperating with said pin 33 to form a cam-follower mechanism.

According to an embodiment, at least one between said first joint 14 and said second joint 17 is a cam joint.

According to an embodiment, at least one between said first joint 14 and said second joint 17 is a clevis joint. According to an embodiment, said clevis joint is formed by two clevis prongs 50 of a link structural body of a link which embraces a portion, and preferably a cylindrical mating portion, of a link structural body of an adjacent link.

According to an embodiment, said pin 33 is realized in separate piece in respect of said first link 6 and said second link 7 and associated to at least two pin seats 34, delimited by said first link distal portion 12 and said second link proximal portion 13, respectively, to form said first joint 14.

According to an embodiment, said pin 33 is realized in separate piece in respect of said second link 7 and said third link 8 and associated to at least two pin seats 34, delimited by said second link distal portion 15 and said third link proximal portion 16, respectively, to form said second joint 17.

According to an embodiment, said pin 33 is in single piece with a link 6 or 7 or 8.

According to an embodiment, said pin 33 is in single piece with a link structural body 9 or 10 or 11.

According to an embodiment, said at least one pin 33 is in single piece with said first link structural body 9 and projects cantilevered from said first link distal portion 12. According to an embodiment, said at least one pin 33 is in single piece with said second link structural body 10 and projects cantilevered from said second link proximal portion 13. According to an embodiment, said at least one pin 33 is in single piece with said second link structural body 10 and projects cantilevered from said second link distal portion 15. According to an embodiment, said at least one pin 33 is in single piece with said third link structural body 11 and projects cantilevered from said third link proximal portion 16.

Figure 19:
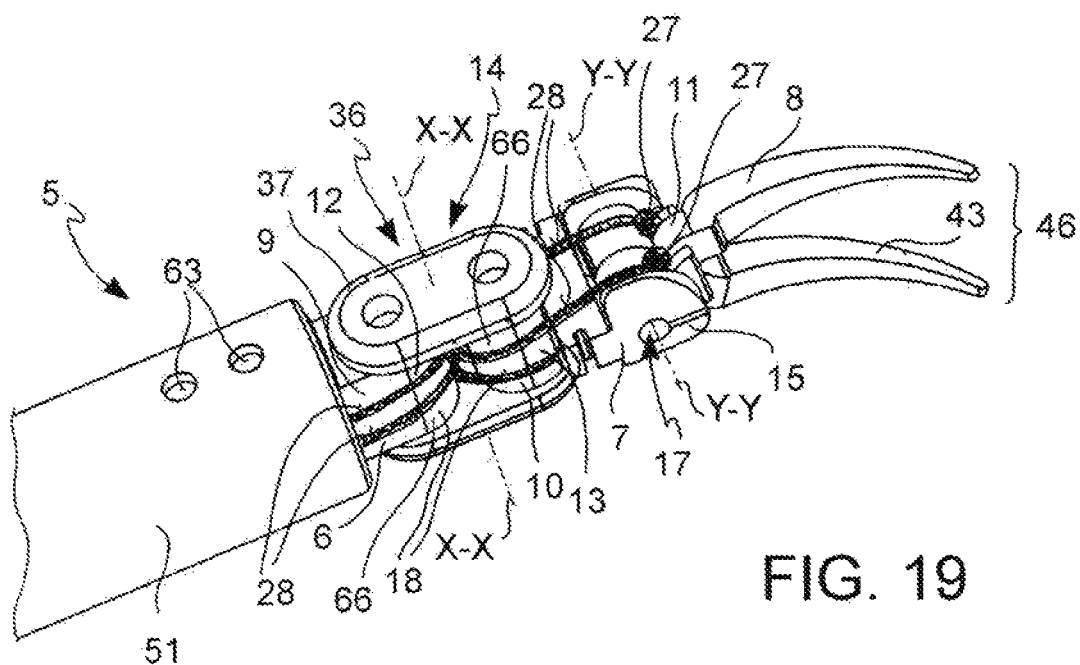
FIG. 19 is a perspective view of a jointed subassembly, according to an embodiment, wherein a double-jointed joint is shown.
Figure 20:
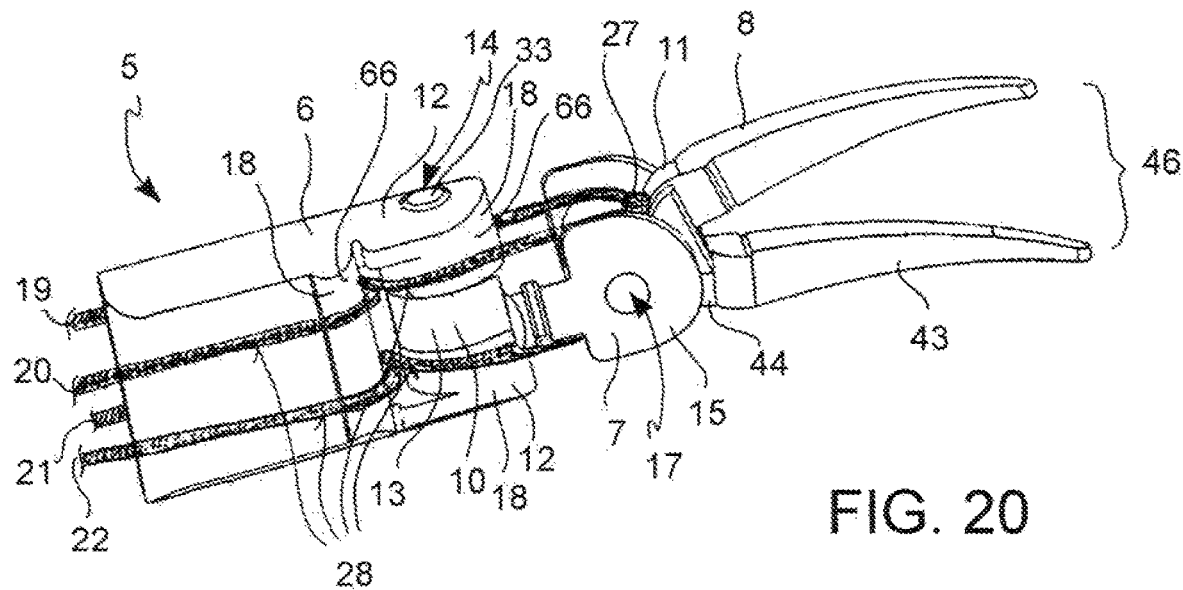
FIG. 20 is a perspective view of a jointed subassembly, according to an embodiment.
Figure 21:
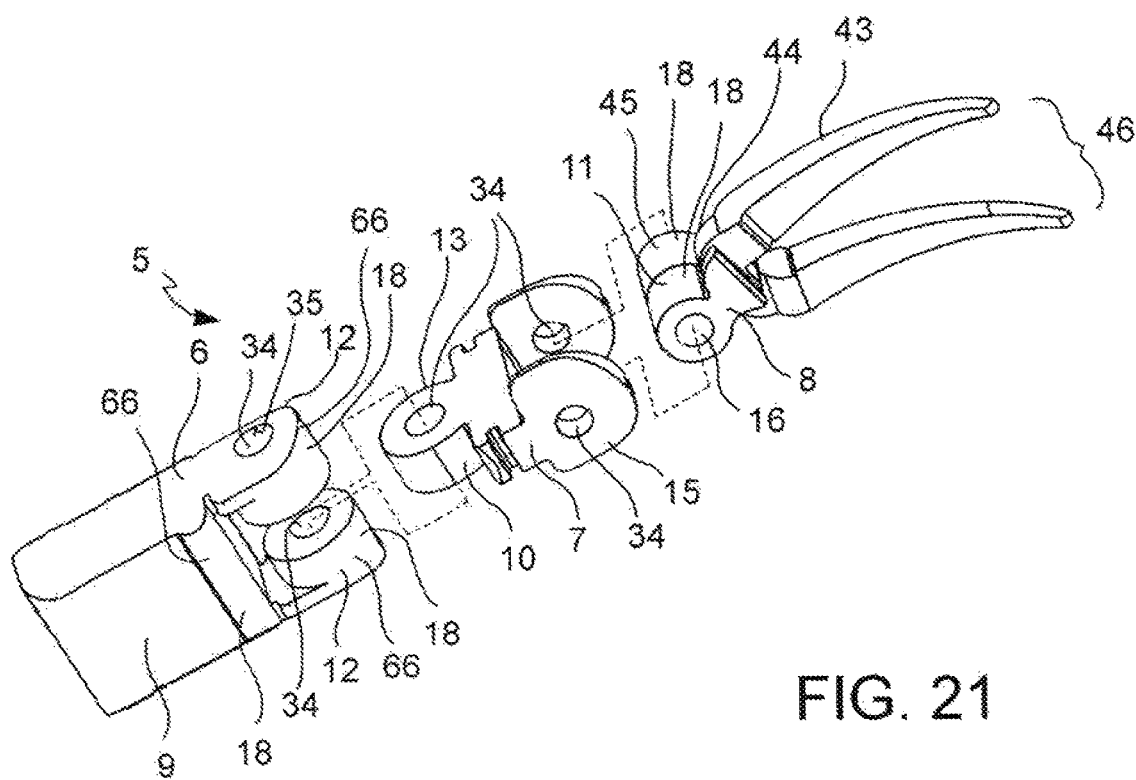
FIG. 21 is an exploded view of the jointed subassembly depicted in FIG. 20, wherein the tendons and the pins are not shown for sought of clarity.
Figure 23:
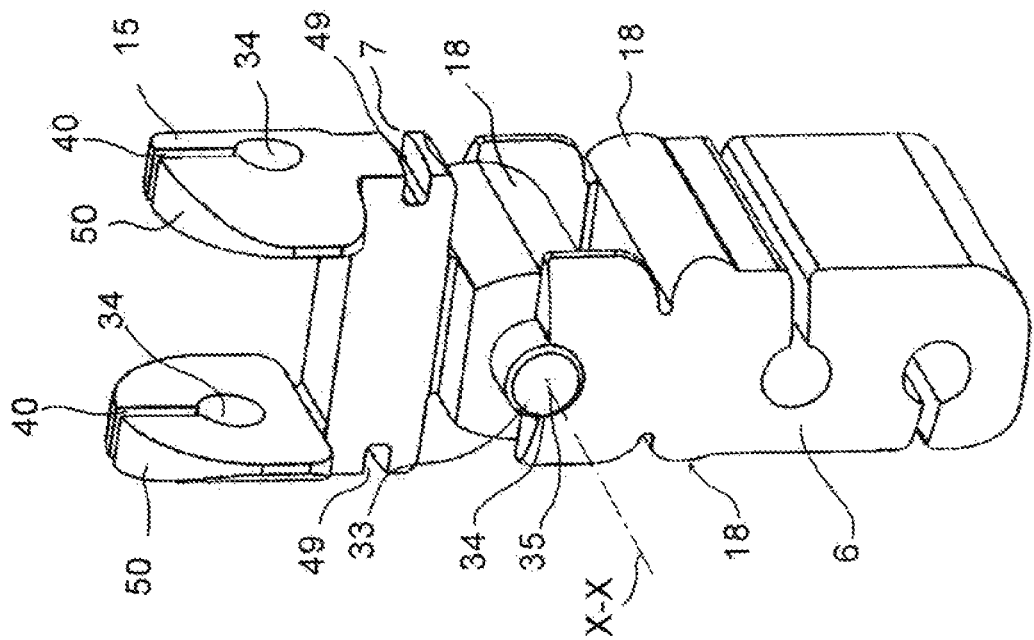
FIG. 23 is a perspective view of a joint of the jointed subassembly, according to an embodiment.
Figure 22:
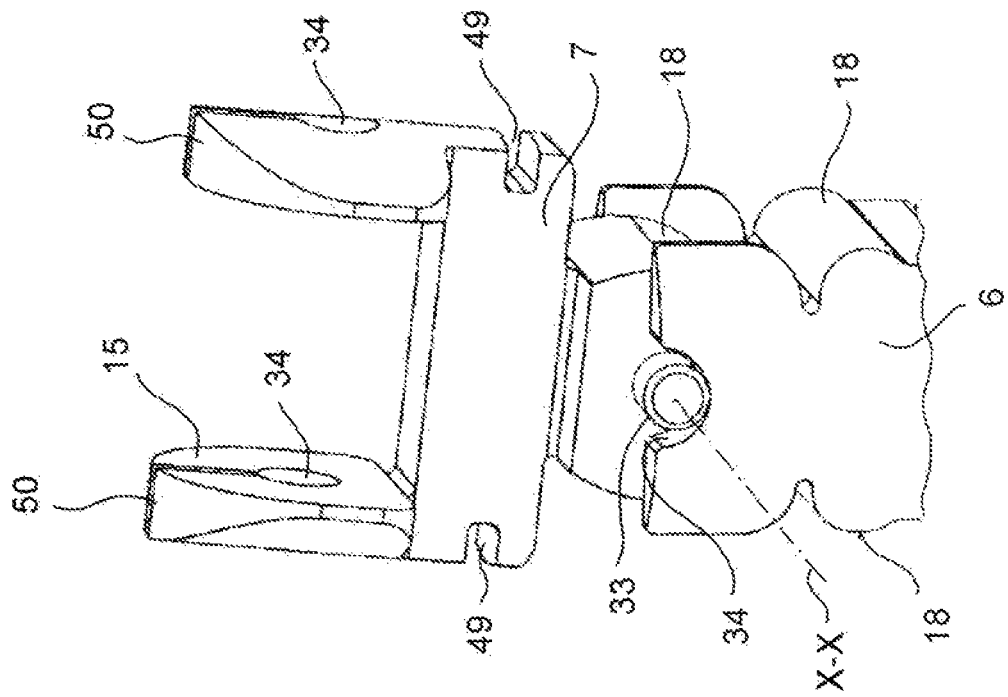
FIG. 22 is a perspective view of a joint of the jointed subassembly, according to an embodiment.

According to an embodiment, for example shown in FIG. 19, at least one between said first joint and said second joint is a double-joined joint 36. Thanks to such double-joined joint 36 is possible to provide a single degree of freedom between two adjacent links, ad detailed described in prior art document U.S. Pat. No. 5,710,870. According to an embodiment, said double-joined joint 36 comprises at least a hinge strut 37 connected to two of said link structural bodies. According to a preferred embodiment, said double-joined joint 36 comprises two opposite hinge struts 37.

According to one embodiment, said double-joined joint 36 is formed by a link and an adjacent link attached to each other via a pair of hinged struts 37. According to one embodiment, said link and said adjacent link pivot about first pivot axis and second pivot axis, wherein a constraining component constrains said link and said adjacent link to rotate with respect to each other. For example, said constraining component can be fixed spurs gears which mesh together or actuation cables routed appropriately. According to an embodiment, said constraining component is said at least one hinged strut 37.

Figure 24:
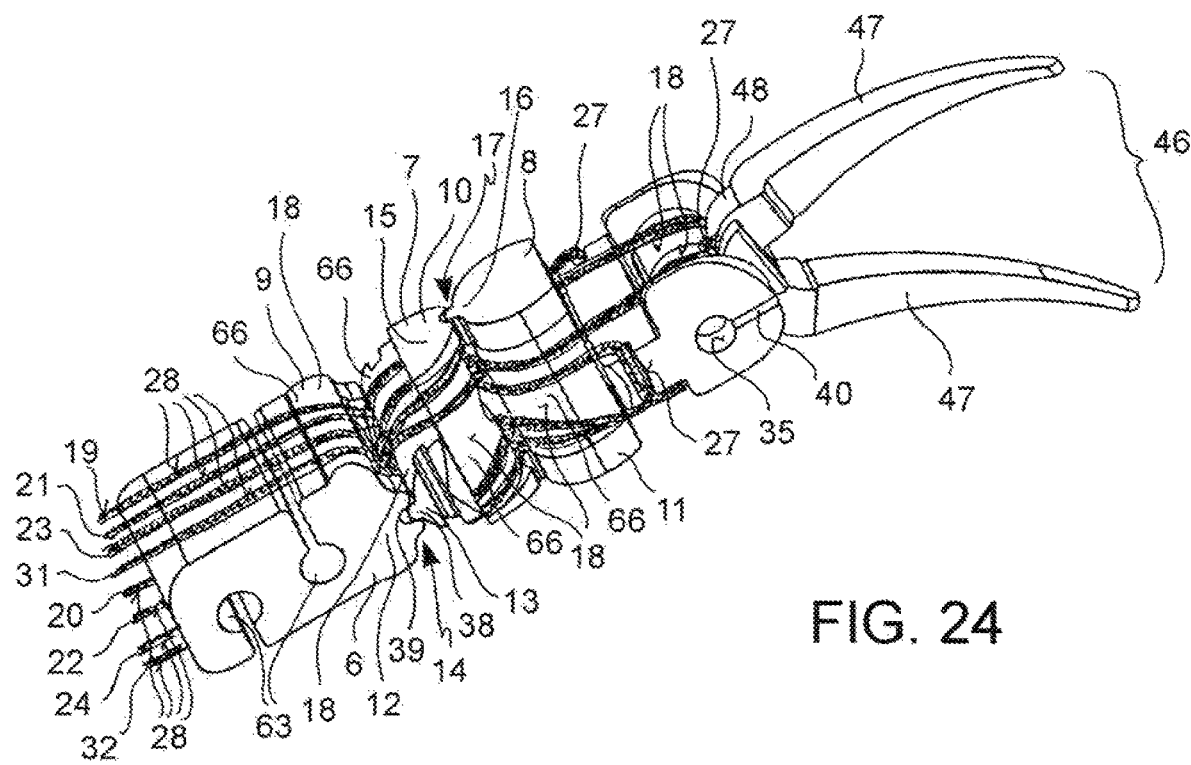
FIG. 24 is a perspective view of a jointed subassembly, according to an embodiment.
Figure 25:
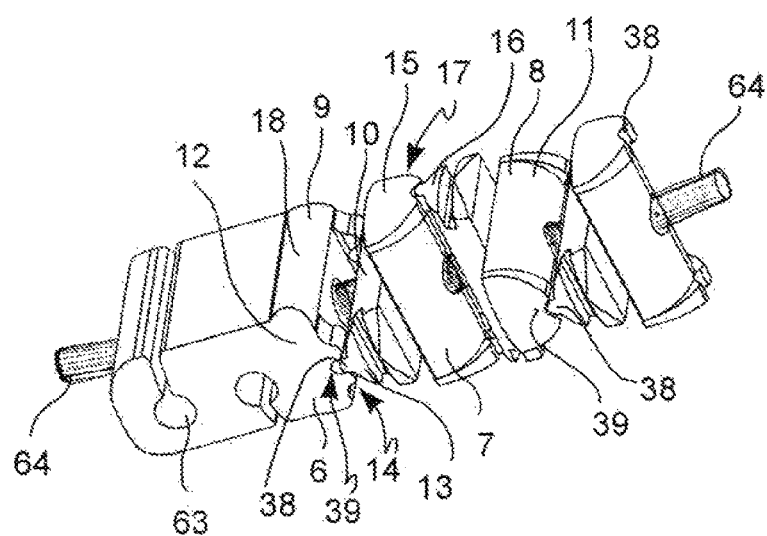
FIG. 25 is a perspective view of a portion of the jointed subassembly shown in FIG. 24, wherein the tendons are not shown for sought of clarity.
Figure 26:
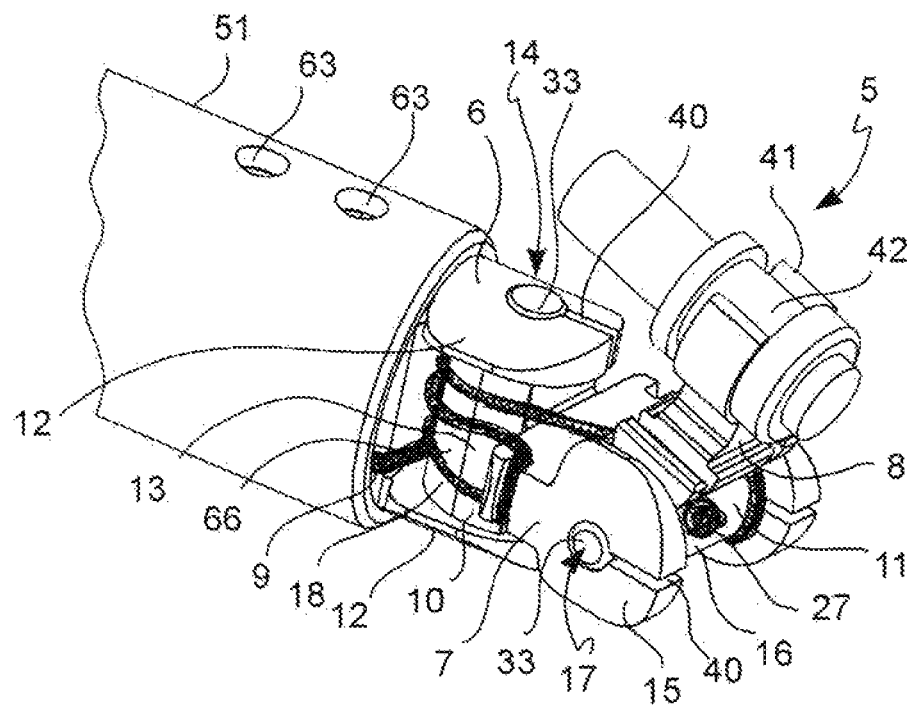
FIG. 26 is a perspective view of a jointed subassembly, according to an embodiment.
Figure 27:
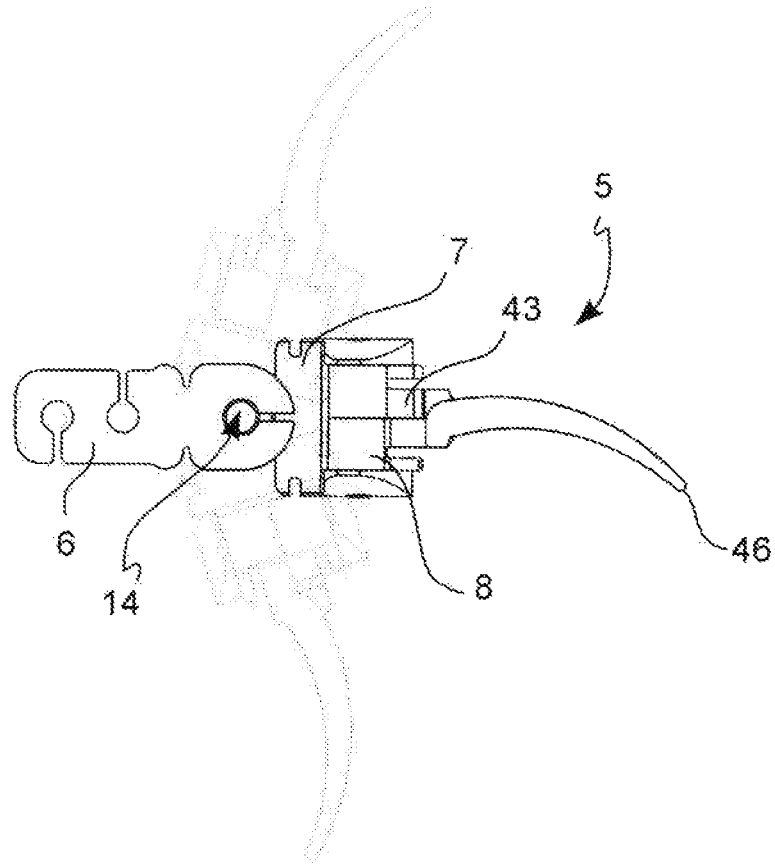
FIG. 27 is a plane views of a jointed subassembly showing three configurations of the jointed subassembly, according to an embodiment.
Figure 28:
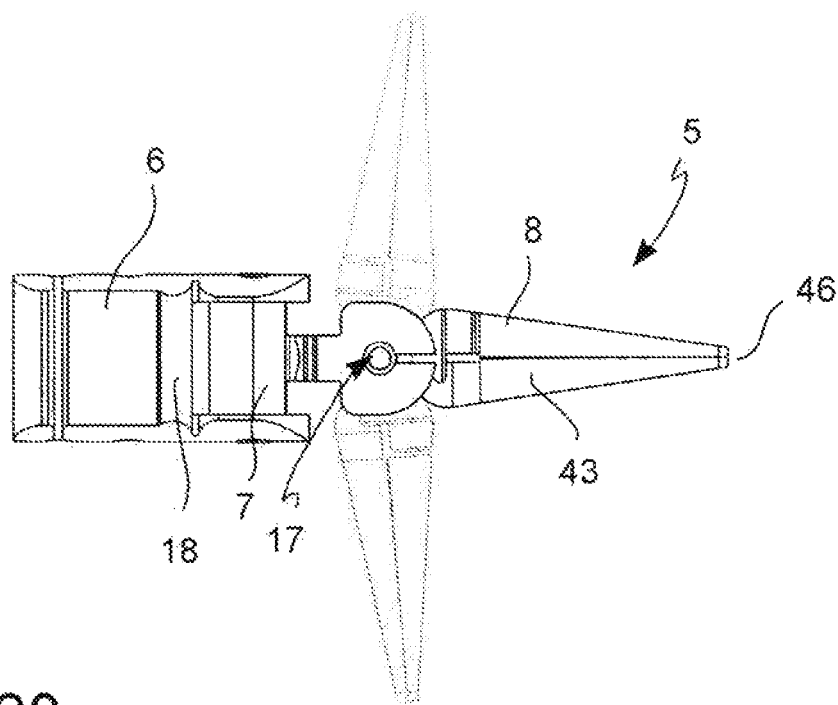
FIG. 28 is a plane views of a jointed subassembly showing three configurations of the jointed subassembly, according to an embodiment.
Figure 29:
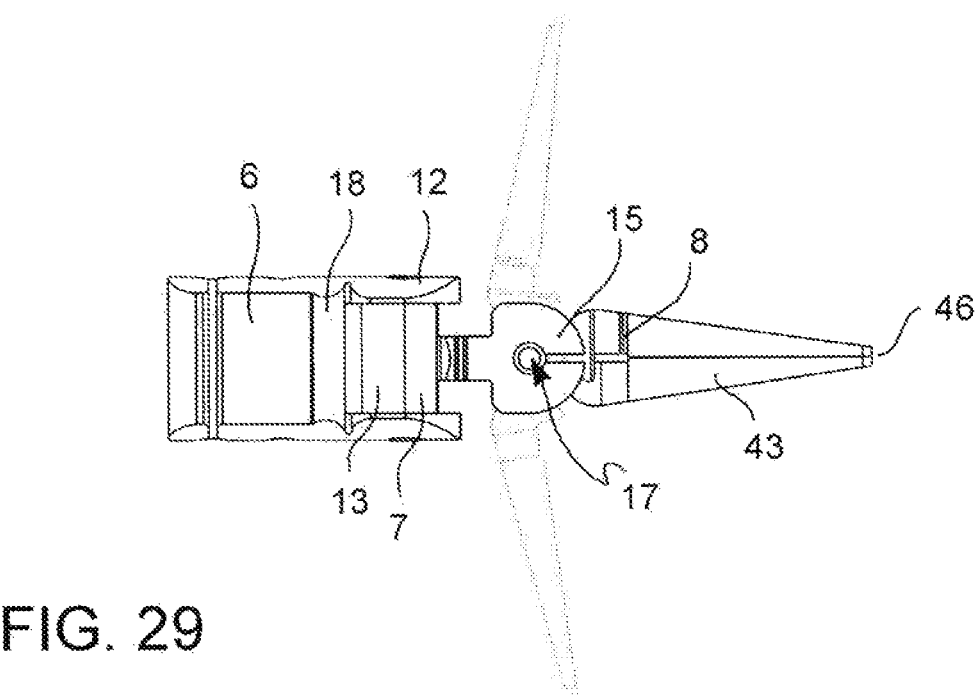
FIG. 29 is a plane views of a jointed subassembly showing three configurations of the jointed subassembly, according to an embodiment.

According to an embodiment, as shown for example in FIGS. 24 and 25, at least one between said first joint 14 and said second joint 17 is formed by opposite joint portions that intermesh one another. According to an embodiment, said first link distal portion 12 delimits at least a joint proximal groove 38 and said first link distal portion 13 comprises at least a joint distal tooth 39, said joint distal tooth 39 cooperates with said joint proximal groove 38 to form said first joint 14. According to an embodiment, said second link distal portion 15 delimits at least a joint proximal groove 38 and said second link distal portion 16 comprises at least a joint distal tooth 39, said joint distal tooth 39 cooperates with said joint proximal groove 38 to form said second joint 17. According to an embodiment, both said joint proximal groove 38 and said joint distal tooth 39 extends substantially parallel to a joint axis.

According to an embodiment, at least one of said links, preferably said third link 8, comprises a C-holder portion 41, suitable for receiving a terminal element 42. For example, said terminal element 42 can be a laser fiber, an irrigation tube, a suction tube or a tissue sensing probe.

According to an embodiment, said jointed subassembly 5 forms at least a portion of an end effector of said surgical instrument 70.

According to an embodiment, said jointed subassembly 5 is a wrist subassembly, wherein said first joint 14 is substantially orthogonal to said second joint 17. According to an embodiment, said jointed subassembly 5 is a wrist subassembly wherein said first joint axis X-X is substantially orthogonal to said second joint axis Y-Y.

According to an embodiment, said jointed subassembly 5 is a elbow subassembly, wherein said first joint 14 is substantially parallel to said second joint 17. According to an embodiment, said jointed subassembly 5 is a elbow subassembly, wherein said first joint axis X-X is substantially parallel to said second joint axis Y-Y.

According to an embodiment, said jointed subassembly 5 comprises a further third link 43 formed of a further third link structural body 44, said further third link structural body 44 being in a single piece.

According to an embodiment, said further third link structural body 44 of said further third link 43 comprises a further third link joint portion 45, said further third link joint portion 45 cooperates with said second link distal portion 15 of said second link structural body 10 of said second link 7 to form a portion of said second joint 17 providing a single degree of freedom between said second link 7 and said further third link 43. In this way, said second joint 17 provides a single degree of freedom between said second link 7 and said third link 8, a single degree of freedom between said second link and said further third link 43, and as a result a single degree of freedom between said third link 8 and said further third link 43.

According to an embodiment, said third link 8 forms a first branch of said kinematic chain and said further third link 43 forms a second a branch of said kinematic chain, wherein said first branch and said second branch are joined in said second joint 17. In this way said kinematic chain is a branched kinematic chain.

According to an embodiment, said third link 8 and said further third link 43 form an instrument tip 46 of said surgical instrument 70. According to an embodiment, said instrument tip 46 has an internal degree of freedom of grasp. According to an embodiment, said instrument tip 46 has at least one yaw degree of freedom in respect of said second link 7.

According to an embodiment, said jointed subassembly 5 comprises at least an additional link 47. According to an embodiment, said at least one additional link 47 is formed of an additional link structural body 48. According to an embodiment, said additional link structural body 48 is jointed to an adjacent link forming an additional joint. For example, said additional link structural body 48 can form an additional joint with a portion of said third link structural body 11. According to an embodiment, said additional link structural body 48 is jointed to an adjacent yet additional link structural body to form a joint.

According to an embodiment, said at least one tendon contact surface 18 is a ruled surface formed by a plurality of straight lines. According to an embodiment, each tendon contact surface 18 is a ruled surface formed by a plurality of straight lines. According to an embodiment, said plurality of straight lines are all parallel to a joint axis X-X or Y-Y. Preferably, said plurality of straight lines are all parallel to the joint axis X-X or Y-Y located closer to said at least one tendon contact surface 18.

According to an embodiment, said at least one tendon contact surface 18 is a convex surface.

According to an embodiment, at least one link structural body among said first structural body 9, said second structural body 10 and said third structural body 11 comprises more than one tendon contact surface 18.

According to an embodiment, all said more than one tendon contact surface 18 are convex surfaces defining with their prolongations thereof a single convex volume. According to an embodiment, the wording "convex volume" means that given a pair of points chosen inside said convex volume, the shorter straight conjunction between them is inside the convex volume in its entirety. This avoids providing grooves or channels on pulleys for guiding the tendons, allowing to further miniaturize the dimensions of the link structural bodies and of the jointed subassembly 5. According to an embodiment, all said more than one tendon contact surfaces 18 of said link structural body of at least one of said links define with their prolongations thereof a link convex hull of said link structural body. According to an embodiment, said link convex hull is defined as the volume comprised within a film wrapping one of said link.

According to an embodiment, said surgical instrument 70 comprises a shaft 51.

According to a preferred embodiment, said first link 6 is directly connected to said shaft 51.

According to an embodiment, said surgical instrument 70 comprises at least a frame 52, suitable for being detachably connected to a portion of said slave manipulator 3. According to an embodiment, said surgical instrument 70 comprises at least a frame 52, suitable for being detachably connected to a actuator compartment of said slave manipulator 3, said actuator compartment hosting said at least one actuator 25 defining a motor compartment 69 or motor box 69. According to an embodiment, said at least one actuator 25 is housed within a portion of said slave manipulator 3.

According to an embodiment, said surgical instrument 70 is detachably associated to said slave manipulator 3.

According to an embodiment, said surgical instrument 70 is associated in a reversible manner to said slave manipulator 3.

According to an embodiment, said shaft 51 extends between said frame 52 and said jointed assembly 5.

According to an embodiment, said shaft 51 is a rigid shaft. According to an embodiment, said shaft 51 has a hollow core that allows the passing of the tendons.

According to an embodiment, said shaft 51 is a flexible shaft. According to an embodiment, said shaft 51 comprises channels to guide at least one of said tendons.

According to an embodiment, said shaft 51 is proximally connected to said frame 52 and distally connected to said first link 6 of said jointed subassembly 5, forming a tubular element connection 61. According to an embodiment, said tubular element connection 61 is a rigid connection, avoiding to provide any degree of freedom between said shaft 51 and said first link 6. According to an embodiment, said tubular element connection 61 comprises at least two tubular element pins 62 inserted in tubular element pin seats 63, preferably holes. Preferably, said tubular element pin seats 63 are at least in number of two, for providing a rigid connection. According to an embodiment, said shaft is distally connected to said first link 6 and the connection includes a solder.

According to an embodiment, said shaft 51 defines a longitudinal shaft axis r-r, substantially coincident to the axis of longitudinal development of said shaft 51. According to an embodiment, said shaft 51 is suitable to rotate around said longitudinal shaft axis r-r to provide a roll motion to the jointed subassembly, in such way to provide said jointed subassembly 5 of a further degree of freedom of roll around said longitudinal shaft axis r-r.

According to an embodiment, said first link structural body 9, said second link structural body 10 and said third link structural body 11 each comprising a passing-through payload hole, and wherein all said passing-through payload holes are substantially aligned one another in such way to be suitable for receive a single payload element 64, preferably extending substantially along said kinematic chain. According to an embodiment, said payload element 64 is one of an irrigation tube, a laser fiber, a cautery wire, a pair of cautery wires, a bending sensing element, avoiding that said payload element 64 is a tendon and/or works as an actuation cable.

According to an embodiment, said tendon distal portion 27 comprises a boss. According to an embodiment, said tendon distal portion 27 comprises a loop. According to an embodiment, said tendon distal portion 27 comprises a knot. According to an embodiment, said tendon distal portion 27 comprises a portion which is glued to a portion of said jointed subassembly 5. According to an embodiment, said tendon distal portion 27 comprises a portion which is wrapped around a portion of a link 6, 7, 8 multiple times. According to an embodiment, said portion which is wrapped around with a curvature radius that is substantially equal to the diameter of the tendon.

According to an embodiment, said tendon proximal portion 26 is glued to a portion of said frame 52. According to an embodiment, said tendon is unraveled into strands around its first tendon proximal portion 26 such as to maximize the glued surface.

According to an embodiment, at least one of said tendons, and preferably each tendon of said tendons, is exclusively suitable to work under tensile load applied at the tendon proximal portion 26 and at the tendon distal portion 27, avoiding said tendon to be pinched, to be laterally guided in a channel or to comprise a sheath.

According to an embodiment, at least one of said tendons, and preferably each tendon of said tendons, is suitable to be pre-lengthened with a load cycle comprising at least two loads of an entity equal to at least half of the tensile breaking strength of said tendon.

According to an embodiment, said slave manipulator 3 comprises at least a micromanipulator, suitable for providing said surgical instrument 70 with three Cartesian degrees of freedom.

According to an embodiment, said at least one actuator 25 comprises at least a pushing element 53 and said surgical instrument 70 comprises, in its proximal frame 52, at least a plunger 54 associated to a tendon, wherein, whenever said surgical instrument 70 is connected with said slave manipulator 3, said pushing element 53 is suitable for pushing against said plunger 54 to determine that the plunger 54 deflects the tendon proximal portion 26 of the tendon associated thereto and to obtain a movement of a link associated to the tendon distal portion of said tendon.

According to an embodiment, a sterile barrier 55 is interposed between said slave manipulator 3 and said surgical instrument 70. According to an embodiment, a sterile barrier 55 is interposed between said at least one pushing element 53 of said slave manipulator 3 and said at least one plunger 54 of said surgical instrument 70. According to an embodiment, said at least one plunger is associated to an elastic element 56 suitable for biasing the plunger against said tendon proximal portion 26 associated thereto. According to an embodiment, said plunger 54 comprises a tendon contact portion 57 which contacts said tendon proximal portion 26. According to an embodiment, said tendon contact portion 57 of said plunger 54 comprises a guide pulley. According to an embodiment, said tendon proximal portion 26 is guided by a plurality of pulleys.

According to an embodiment, said surgical instrument 70 comprises a jointed subassembly 5 comprising at least a first link 6, a second link 7 and a third link 8.

According to an embodiment, said first link 6 and said second link 7 are associated in a first joint 14 providing a degree of freedom between said first link 6 and said second link 7.

According to an embodiment, said second link 7 and said third link 8 are associated in a second joint 17 providing a degree of freedom between said second link 7 and said third link 8.

According to an embodiment, said surgical instrument 70 comprises at least a tendon 19 for moving a degree of freedom.

According to an embodiment, said at least one tendon 19 is suitable for moving said third link 8 in respect of at least said second link 7. According to an embodiment, said surgical instrument 70 comprises at least a pair of tendons 19, 20 for moving a degree of freedom. According to an embodiment, said pair of tendons 19, 20 is suitable for moving said third link 8 in respect of at least said second link 7.

According to a preferred embodiment, said tendon 19 comprises a tendon proximal portion 26, suitable to be associated to at least an actuator 25 not placed in said jointed subassembly 5, a tendon distal portion 27, secured to said third link 8, and a tendon intermediate portion 28, extending between said tendon proximal portion 26 and said tendon distal portion 27. For example, said at least one actuator 25 is located in an actuator compartment 69 portion of said slave manipulator 3 placed upstream with respect of the jointed subassembly 5.

According to an embodiment, at least one between said first link 6 and said second link 7 comprises at least one tendon contact surface 18 on which said tendon 19, and preferably said tendon intermediate portion 28, slides remaining in contact with said at least one tendon contact surface 18, defining one or more sliding paths 65 on said at least one tendon contact surface 18. In this way said at least one tendon contact surface 18 is a tendon sliding surface 66.

According to a preferred embodiment, said at least one tendon contact surface 18 of either said first link 6 and said second link 7 is a smooth surface having a surface profile without sharp edges.

According to a preferred embodiment, said at least one tendon contact surface 18 of either said first link 6 and said second link 7 is a tendon sliding surface 66, on which said tendon 19 slides remaining in contact with said at least one tendon sliding surface 66. In other words, according to an embodiment, said at least one tendon contact surface 18 on which said tendon intermediate portion slides, is a tendon sliding surface 66. According to an embodiment, said third link 8 comprises at least one tendon contact surface 18 and said tendon touches said tendon contact surface 18 of said third link 8 avoiding to slide thereon. According to an embodiment, said tendon distal portion 27 is unsuitable for sliding on a tendon contact surface 18.

According to an embodiment, said sliding path 65 has substantially a prevailing longitudinal extension. According to an embodiment, said sliding path 65 is the imprint that the tendon 19 defines on said tendon contact surface 18. According to a preferred embodiment, each of said one or more sliding paths 65 is a continuous path. According to an embodiment, said tendon 19 and said tendon contact surface 18 exchange local frictional forces as a result of the local relative motion. According to an embodiment, said tendon slides on said at least one tendon contact surface 18 along, or parallel to, the direction of its longitudinal development T-T, or tendon longitudinal path T-T. According to an embodiment, said tendon avoid to slide on said at least one tendon contact surface 18 in a direction transversal to the tendon longitudinal path T-T. According to an embodiment, said tendon longitudinal path T-T is stationary over the time. According to an embodiment, said one or more sliding paths 65 are coincident or parallel to a portion of said tendon longitudinal path T-T.

According to an embodiment, said sliding path 65 comprises and proximal or initial sliding path end, characterized by an initial tendon path direction immediately before said initial sliding path end, and a distal or final sliding path end, characterized by an final tendon path direction immediately after said final sliding path end. According to an embodiment, said tendon intermediate portion 28 is deflected by said at least one of first link 6 and second link 7. According to an embodiment, said tendon intermediate portion 28 is deflected by said at least one of first link 6 and second link 7 from an initial tendon path direction to final tendon path direction. According to an embodiment, said tendon intermediate portion is deflected by said at least one of first link 6 and second link 7 by a tendon deflection angle. According to an embodiment, said tendon deflection angle is measured as the angle between said initial tendon path direction and said final tendon path direction. According to an embodiment, said tendon intermediate portion is deflected by said at least one of first link 6 and second link 7 by one or more tendon deflection angles. According to an embodiment, a total deflection angle is the sum of all said tendon deflection angles. According to an embodiment, in at least one configuration of said jointed subassembly 5, said total deflection angle α+ß is equal to or greater than 120 degrees. According to an embodiment, a straight configuration of said jointed subassembly has said link 2 and 3 at the center of their joint range of motion. According to an embodiment, in said straight configuration of said jointed subassembly 5, said total deflection angle α+ß is equal to or greater than 90 degrees.

According to a preferred embodiment, said total tendon deflection angle α+ß is said total winding angle α+ß.

According to a preferred embodiment, said at least one tendon longitudinal path T-T is tangent to said at least one tendon contact surface 18 of either said first link 6 and said second link 7 at said initial sliding path end. According to a preferred embodiment, said at least one tendon longitudinal path T-T is tangent to said at least one tendon contact surface 18 of either said first link 6 and said second link 7 at said final sliding path end. According to a preferred embodiment, for every jointed assembly configuration, said at least one tendon longitudinal path T-T is a smooth continuous curve, without angles.

According to an embodiment, the sum of all the sliding paths 65 of all the tendon contact surfaces 18 defines a total winding angle α+ß.

According to an embodiment, the sum of all the sliding paths 65 of all the tendon contact surfaces 18 sweeps a total winding angle α+ß. According to an embodiment, the sum of all the sliding paths 65 of all the tendon contact surfaces 18 is covered by a total winding angle α+ß.

According to an embodiment, a single sliding path of a tendon contact surface 18 of one link between said first link 7 and said second link 8 defines a local winding angle α or ß. According to an embodiment, the sum of all said local winding angles defines said total winding angle α+ß. According to an embodiment, a single sliding path 65 of a tendon contact surface 18 of one link between said first link 7 and said second link 8 defines a first local winding angle α. According to an embodiment, a single sliding path 65 of a tendon contact surface 18 of one link between said first link 7 and said second link 8 defines a second local winding angle ß.

According to an embodiment, in at least one configuration of said jointed subassembly 5, said total winding angle α+ß is equal to or greater than 120 degrees.

According to an embodiment, in said straight configuration of said jointed subassembly 5, said total winding angle α+ß is equal to or greater than 90 degrees.

According to an embodiment, the term "configuration" indicates a spatial geometrical positioning of said jointed subassembly 5. According to an embodiment, the term "configuration" indicates the relative spatial positioning and orientation of the links 6, 7, 8 forming said jointed subassembly 5.

According to an embodiment, one between said first link 6 and said second link 7 comprises at least two tendon contact surfaces 18, on which said tendon 19, and preferably said tendon intermediate portion 28, slides remaining in contact with both said at least two tendon contact surface 18, defining said one or more sliding paths 65 on said at least two tendon contact surfaces 18.

According to an embodiment, said first link 7 comprises at least one tendon contact surfaces 18, on which said tendon 19, and preferably said tendon intermediate portion 28, slides remaining in contact with said at least one tendon contact surface 18, defining said one or more sliding paths 65 on said at least one tendon contact surface 18, and said second link 8 comprises at least one further tendon contact surfaces 18, on which said tendon 19, and preferably said tendon intermediate portion 28, slides remaining in contact with said at least one further tendon contact surface 18, defining said one or more sliding paths 65 on said at least one further tendon contact surface 18.

According to an embodiment, said jointed subassembly 5 comprises at least two tendon contact surfaces 18 being said tendon sliding surfaces 66, on which said tendon 19, and preferably said tendon intermediate portion 28, slides remaining in contact with both said at least two tendon sliding surfaces 66, defining said one or more sliding paths 65 on said at least two tendon sliding surfaces 66.

According to an embodiment, said third link 8 comprises at least a tendon contact surface 18 which is unsuitable for said tendon 19, and preferably for said tendon distal portion 27, to slide thereon.

According to an embodiment, each of said local winding angles is defined as the angle subtended to said tendon contact surface 18. According to an embodiment, said total winding angle α+ß is defined as the sum of all said local winding angles.

According to an embodiment, each of said local winding angles is defined as the angle formed by the two orthogonal lines to said tendons directed along said tendon longitudinal path T-T and defined in portions of said tendons that delimits the contact path 65 on said tendon contact surface 18.

According to an embodiment, each of said local winding angles is defined as the angle formed by the two tendon longitudinal path T-T directions and defined in portions of said tendons that delimits the contact path 65 on said tendon contact surface 18.

According to an embodiment, said at least one tendon contact surface 18 comprises a proximal contact surface border 67 and a distal contact surface border 68 which delimit said tendon contact surface 18 along said tendon longitudinal path T-T, wherein said proximal contact surface border 67 is located proximally in respect of said distal contact surface border 68. According to an embodiment, each of said local winding angles is defined as the angle formed by the orthogonal lines to said tendon longitudinal path T-T evaluated immediately before said proximal contact surface border 67 and said tendon longitudinal path T-T evaluated immediately after said distal contact surface border 68.

According to an embodiment, said at least one tendon contact surface 18 comprises a proximal contact surface border 67 and a distal contact surface border 68 which delimit said tendon contact surface 18 along said tendon longitudinal path T-T, wherein said proximal contact surface border 67 is located proximally in respect of said distal contact surface border 68. According to an embodiment, each of said local winding angles is defined as the angle formed by said tendon longitudinal path T-T direction evaluated immediately before said proximal contact surface border 67 and said tendon longitudinal path T-T direction evaluated immediately after said distal contact surface border 68.

According to an embodiment, each local winding angle α or ß is defined on a surface on which said tendon slides while remaining in contact, even if said surface is discontinuous or has sharp points.

According to an embodiment, each local winding angle α or ß is measured with reference to the center of the oscillator circle to a single tendon contact surface 18.

According to an embodiment, all contact points of a single tendon sliding surface 18 of a link embraces a portion of said link in such way to define a local winding angle α or ß.

According to an embodiment, said total winding angle α+ß is comprised between 60 degrees and 300 degrees.

According to an embodiment, said total winding angle α+ß is comprised between 90 degrees and 270 degrees.

According to an embodiment, each link 6, 7, 8 has a link encumber. According to an embodiment, said at least one tendon contact surface 18 delimits at least partially said link encumber of a link.

According to an embodiment, said tendon contact surface 18 is cylindrical. According to an embodiment, said tendon contact surface 18 is a portion of a cylindrical surface.

According to a preferred embodiment, said tendon is made of polymeric material.

According to an embodiment, said tendon is made of a material chosen in the group consisting of polyethylene, ultra-high molecular weight polyethylene or UHMWPE, Kevlar®, Vectran®, Zylon®, polybenzobisoxazole, carbon fibers and combination thereof.

According to a preferred embodiment, said tendon intermediate portion 28 is made of polymeric material. In this way, it is possible to provide said tendon intermediate portion 28 with less friction, less wear over the life time, thus less upkeep, and it is possible to realize said tendon intermediate portion 28 having inferior diameter in respect of tendons in other materials.

According to an embodiment, said tendon intermediate portion 28 is made of a material chosen in the group consisting of polyethylene, ultra-high molecular weight polyethylene or UHMWPE, Kevlar®, Vectran®, Zylon®, polybenzobisoxazole, carbon fibers and combination thereof.

According to an embodiment, said at least one tendon contact surface 18 is made of a material chosen in the group consisting of: steel, ceramic, titanium, liquid metal, and combination thereof.

According to an embodiment, said at least one tendon sliding surface 66 is made of a material chosen in the group consisting of: steel, ceramic, titanium, liquid metal, and combination thereof.

According to a preferred embodiment, said tendon intermediate portion 28 is made of ultra-high molecular weight polyethylene and said at least one tendon contact surface 18 is made of steel alloy. According to a preferred embodiment, said tendon is made of ultra-high molecular weight polyethylene and said at least one tendon contact surface 18 is made of steel. In this way, it is possible to obtain a friction coefficient in the range 0.04 to 0.08. In this way, stiction of the tendon intermediate portion 28 is avoided.

According to an embodiment, the dry sliding friction between said tendon contact surface 18 and said tendon intermediate portion 28 has a friction coefficient equal to or lower than 0.1. For example, the dry sliding friction of such a tendon intermediate portion 28 over such tendon contact surface 18 is more than five times less that the dry sliding friction defined by a metal tendon intermediate portion sliding over a metal tendon sliding surface that will result in the latter case to have a friction coefficient equal to substantially 0.5.

According to a preferred embodiment, said friction coefficient is lower than 0.1.

According to an embodiment, said total winding angle is substantially equal to 360 degrees. It is worth noting that the total friction in a tendon sliding over a tendon sliding surface over a winding angle is proportional to the tendon tension multiplied by the exponential of the product between the friction coefficient and the winding angle. Thus a reduction of the friction coefficient allows to employ a proportionally larger winding angle. Being able to employ a larger winding cable opens up the possibility to route the tendons over the link structural bodies, avoiding the use of tendon guiding elements difficult to miniaturize.

According to an embodiment, the encumber of said links 6, 7 8 has a maximum extension, in a direction transversal to the longitudinal extension of said jointed subassembly 5 equal to or lower than 8 millimeters, and preferably equal to or lower than 5 millimeters, and preferably measuring in range from 2 millimeters to 5 millimeters.

According to an embodiment, said jointed subassembly 5 fits in its entirety in a cylindrical volume having a diameter measuring in range from 2 millimeters to 5 millimeters.

According to a preferred embodiment, said tendon intermediate portion 28 has a diameter equal to or lower than 0.5 millimeters and preferably comprised between 0.005 millimeters and 0.5 millimeters.

According to an embodiment, said tendon has a substantially circular cross section. According to an embodiment, the diameter of said tendon is variable in different portions of said tendon. According to an embodiment, the mechanical properties of said tendon are variable in different portions of said tendon. According to an embodiment, said tendon is obtained by joining portions of tendons with different characteristics. According to an embodiment, said tendon is connected to a stiffening rod element in the straight section running inside the shaft hollow core. According to an embodiment, said tendon is obtained by joining portions of tendons with different characteristics.

According to an embodiment, said master tool 2 is associated to a master interface. According to an embodiment, said control unit 4 controls a master control unit that controls at least one slave control unit.

According to a general embodiment, it is provided a surgical instrument 70 according to any one of the embodiments previously described.

According to a general embodiment, it is provided a slave assembly comprising at least a slave manipulator 3 according to any one of the embodiments previously described and at least a surgical instrument 70 according to any one of the embodiments previously described.

By virtue of the features described above, provided either separately or in combination, where applicable, in particular embodiments, it is possible to satisfy the sometimes contrasting needs disclosed above, and to obtain the aforesaid advantages, and in particular:

it is provided a miniaturization of surgical instrument;

it is provided a solution having at least three link structural bodies directly connected in series to form a kinematic chain;

it is possible to actuate a degree of freedom of said jointed subassembly by means of a tendon including a tendon intermediate portions contacting the links only in the above defined tendon contact surfaces, thus avoiding to provide channels or through holes or pulleys to guide said tendon intermediate portions, while keeping said tendon intermediate portions close to said jointed subassembly for all configuration of said jointed subassembly and while allowing said tendon to pull on said links with a uniform mechanical advantage for all configuration of said jointed subassembly.

Those skilled in art may make many changes and adaptations to the embodiments described above or may replace elements with others which are functionally equivalent in order to satisfy contingent needs without however departing from the scope of the appended claims.

LIST OF REFERENCES 1 microsurgery assembly
2 Master tool
3 Slave or slave manipulator
4 Control unit
5 Jointed subassembly
6 First link
7 Second link
8 Third link
9 First link structural body or structural body of said first link
10 Second link structural body or structural body of said second link
11 Third link structural body or structural body of said
12 First link distal portion of said first link structural body
13 Second link proximal portion of said second link structural body
14 First joint
15 Second link distal portion of said second link structural body
16 Third link proximal portion of said third link structural body
17 Second joint
18 Tendon contact surface
19, 20, 21, 22, 23, 24, 30, 31 Tendons
25 Actuator
26 Tendon proximal portion
27 Tendon distal portion
28 Tendon intermediate portion
29 Patient
30 Surgeon
33 Pin
34 Pin seat
35 Pin seat boundary
36 Double-joined joint
37 Hinge strut
38 Joint proximal groove
39 Joint distal tooth
40 Cavity mouth
41 c-holder portion
42 Terminal element
43 Further third link
44 Further third link structural body
45 Further third link joint portion
46 Instrument tip
47 Additional link
48 Additional link structural body
49 Tendon securing portion
50 Clevis prong
51 Shaft
52 Frame
53 Pushing element
54 plunger
55 Sterile barrier
56 Elastic element
57 Tendon contact portion of the plunger
58 Actuator drive unit
59 First command signal
60 Second command signal
61 Tubular element connection
62 Tubular element pin
63 Tubular element pin seat
64 Payload element
65 Sliding path
66 Tendon sliding surface
67 Proximal contact surface border
68 Distal contact surface border
69 Motor box or motor compartment
70 Medical Instrument or Surgical Instrument or Instrument
X-X First joint axis
Y-Y Second joint axis
r-r Longitudinal direction of the shaft
T-T Tendon longitudinal path
$\alpha$ Local winding angle or first local winding angle
ß Local winding angle or second local winding angle
$\alpha$+ß Total winding angle

The invention claimed is:

1. A robotic microsurgery assembly comprising:
at least one master tool, to detect a manual command;
at least one slave manipulator;
at least one surgical instrument operated on by said at least one slave manipulator;
at least one control unit configured to receive at least a first command signal comprising information about said manual command and to send a second command signal to at least one actuator to control said slave manipulator;
wherein said surgical instrument comprises at least one jointed subassembly; said jointed subassembly comprising a first link, a second link, and a third link;
wherein:
said first link is formed of a first link structural body, said first link structural body being a single piece;
said second link is formed of a second link structural body, said second link structural body being a single piece;
said third link is formed of a third link structural body, said third link structural body being a single piece; and
wherein:
said first link structural body comprises a first link distal portion forming a first joint proximal portion and said second link structural body comprises a second link proximal portion forming a first joint distal portion; said first link distal portion and said second link proximal portion cooperating to form at least partially a first joint providing a single degree of freedom between said first link and said second link;
said second link structural body further comprises a second link distal portion forming a second joint proximal portion and said third link structural body comprises a third link proximal portion forming a second joint distal portion, said second link distal portion and said third link proximal portion cooperate to form at least partially a second joint providing a single degree of freedom between said second link and said third link;

and wherein said surgical instrument comprises at least three tendons, each tendon of said at least three tendons comprising:
- a tendon proximal portion, associated to said at least one actuator;
- a tendon distal portion, secured to and extending over said second link or to said third link;
- a tendon intermediate portion, extending between said tendon proximal portion and said tendon distal portion;
- wherein said tendon intermediate portion of at least two of said tendons contacts said jointed subassembly exclusively in at least one tendon contact surface of said first link structural body and in at least one tendon contact surface of said second link structural body;
- avoiding said at least one tendon contact surface of the first link structural body and said at least one tendon contact surface of said second link structural body being a hole surface.

2. Robotic microsurgery assembly according to claim 1, wherein
each of said first link structural body, said second link structural body and said third link structural body comprises at least one tendon contact surface.

3. Robotic microsurgery assembly according to claim 1, wherein each tendon contact surface is a ruled surface formed by a plurality of straight lines; and/or
wherein said plurality of straight lines are all parallel to a joint axis.

4. Robotic microsurgery assembly according to claim 1, wherein said tendon contact surfaces are outer surfaces of said link structural bodies.

5. Robotic microsurgery assembly according to claim 1, wherein said tendon contact surfaces are convex surfaces.

6. Robotic microsurgery assembly according to claim 1, wherein said jointed subassembly is a wrist subassembly, wherein said first joint is substantially orthogonal to said second joint.

7. Robotic microsurgery assembly according to claim 1, wherein said jointed subassembly is an elbow subassembly, wherein said first joint is substantially parallel to said second joint.

8. Robotic microsurgery assembly according to claim 1, wherein at least two of said tendons contact a same tendon contact surface.

9. Robotic microsurgery assembly according to claim 1, wherein at least one between said first joint and said second joint:
is a pin joint, comprising at least one pin and at least one pin seat for receiving said at least one pin; and/or
is formed by opposite joint portions intermeshing one another.

10. Robotic microsurgery assembly according claim 1, wherein at least one between said first joint and said second joint:
is a cam joint; and/or
is a rolling joint; and/or
is a double-joined joint; and/or
is a clevis joint.

11. Robotic microsurgery assembly according to claim 1, wherein one between said first link and said second link comprises at least two tendon contact surfaces, on which said tendon intermediate portion of at least one of said tendons slides remaining in contact with both said at least two tendon contact surfaces, defining said one or more sliding paths on said at least two tendon contact surfaces.

12. Robotic microsurgery assembly according to claim 11, wherein said tendon intermediate portion of each tendon of said tendons contacts said jointed subassembly exclusively in said at least one tendon contact surface of at least two among said first link structural body, said second link structural body and said third link structural body.

13. Robotic microsurgery assembly according to claim 1, wherein said at least one tendon contact surface avoids delimiting a through hole in a link structural body; and/or
wherein a normal line orthogonal to said at least one tendon contact surface avoids intersecting the structural body comprising said at least one tendon contact surface; and/or
wherein said tendon contact surface avoids facing the same tendon contact surface; and/or
wherein said tendon contact surface urges said tendon intermediate portion away from the link structural body comprising said tendon contact surface; and/or
wherein said tendon contact surface embraces one of said tendon over an angle equal to or lower than 180 degrees; and/or
wherein said tendon contact surface is an outer surface of one of said link structural bodies; and/or
wherein said tendon contact surface delimits at least partially an encumber of one of said link structural bodies; and/or
wherein each tendon comprises a first longitudinal side and a second opposite longitudinal side, wherein one between said first longitudinal side and said second longitudinal side is in contact with at least one of said links, wherein when said first longitudinal side is in contact with a link, said first longitudinal side faces away from said link; and/or wherein
each of said first longitudinal side and said second opposite longitudinal side covers on said tendon an angle of substantially 180 degrees while remaining disjointed one another.

* * * * *